United States Patent
Sengstaken, Jr.

(10) Patent No.: US 10,438,476 B2
(45) Date of Patent: Oct. 8, 2019

(54) WIRELESS HAND HYGIENE TRACKING SYSTEM AND RELATED TECHNIQUES

(71) Applicant: Vypin, LLC, Alpharetta, GA (US)

(72) Inventor: Robert William Sengstaken, Jr., Hollis, NH (US)

(73) Assignee: VYPIN, LLC, Alpharetta, GA (US)

( * ) Notice: Subject to any disclaimer, the term of this patent is extended or adjusted under 35 U.S.C. 154(b) by 0 days.

(21) Appl. No.: 15/597,874

(22) Filed: May 17, 2017

(65) Prior Publication Data

US 2017/0256155 A1   Sep. 7, 2017

Related U.S. Application Data

(63) Continuation-in-part of application No. 14/304,195, filed on Jun. 13, 2014, now Pat. No. 10,121,028.

(60) Provisional application No. 62/337,846, filed on May 17, 2016, provisional application No. 61/839,561, filed on Jun. 26, 2013, provisional application No. 61/902,316, filed on Nov. 11, 2013, provisional (Continued)

(51) Int. Cl.
| | |
|---|---|
| *G08B 21/24* | (2006.01) |
| *G06Q 10/06* | (2012.01) |
| *G06F 19/00* | (2018.01) |
| *G16H 40/20* | (2018.01) |
| *G06K 7/10* | (2006.01) |
| *G06K 19/07* | (2006.01) |

(52) U.S. Cl.
CPC ....... *G08B 21/245* (2013.01); *G06F 19/3418* (2013.01); *G06K 7/10009* (2013.01); *G06K 19/0702* (2013.01); *G06K 19/0716* (2013.01); *G06K 19/0717* (2013.01); *G06K 19/0723* (2013.01); *G06Q 10/06398* (2013.01); *G16H 40/20* (2018.01)

(58) Field of Classification Search
CPC .................................................... G08B 21/245
USPC ...................................................... 340/573.1
See application file for complete search history.

(56) References Cited

U.S. PATENT DOCUMENTS

| | | |
|---|---|---|
| 4,617,557 A | 10/1986 | Gordon |
| 4,823,982 A | 4/1989 | Aten et al. |

(Continued)

FOREIGN PATENT DOCUMENTS

| | | |
|---|---|---|
| KR | 1020110103340 A | 9/2011 |
| WO | 2013023804 A1 | 2/2013 |

*Primary Examiner* — Qutbuddin Ghulamali
(74) *Attorney, Agent, or Firm* — Hayes Soloway PC

(57) ABSTRACT

A wireless hand hygiene compliance tracking system and related techniques are disclosed. The system may include one or more micro-zone (mZone) transmitters configured to be deployed at designated locations where hand hygiene compliance is desired. A given mZone transmitter may transmit an mZone signal including data pertaining to its type and identity, from which its purpose and location may be derived. A monitored individual may host a beacon tag configured to receive the mZone signal and pull mZone type and identification data therefrom, relaying that data in its own beacon signal, along with current hand hygiene compliance or non-compliance status data. The beacon tag may be programmed with one or more hand hygiene compliance modes selectable based on the desired monitoring context. The beacon signal may be received by any gateway or reader device within transmission range. In this manner, compliant and non-compliant events may be tracked.

23 Claims, 12 Drawing Sheets

Related U.S. Application Data application No. 61/902,325, filed on Nov. 11, 2013, provisional application No. 61/974,770, filed on Apr. 3, 2014.

(56) References Cited

U.S. PATENT DOCUMENTS

| | | | |
|---|---|---|---|
| 4,922,433 | A | 5/1990 | Mark |
| 5,014,851 | A | 5/1991 | Wick |
| 5,323,907 | A | 6/1994 | Kalvelage |
| 5,412,372 | A | 5/1995 | Parkhurst et al. |
| 5,791,478 | A | 8/1998 | Kalvelage et al. |
| 5,852,590 | A | 12/1998 | de la Huerga |
| 5,990,647 | A | 11/1999 | Zettler |
| 6,052,093 | A | 4/2000 | Yao et al. |
| 6,188,678 | B1 | 2/2001 | Prescott |
| 6,244,462 | B1 | 6/2001 | Ehrensvard et al. |
| 6,310,555 | B1 | 10/2001 | Stern |
| 6,325,066 | B1 * | 12/2001 | Hughes .............. A61F 5/48 128/885 |
| 6,411,567 | B1 | 6/2002 | Niemiec |
| 6,542,114 | B1 | 4/2003 | Eagleson et al. |
| 6,574,166 | B2 | 6/2003 | Niemiec |
| 6,720,888 | B2 | 4/2004 | Eagleson et al. |
| 7,113,101 | B2 | 9/2006 | Peterson et al. |
| 7,142,123 | B1 | 11/2006 | Kates |
| 7,221,280 | B2 | 5/2007 | Hsieh |
| 7,263,875 | B2 | 9/2007 | Hawk |
| 7,352,286 | B2 | 4/2008 | Chan et al. |
| 7,394,381 | B2 | 7/2008 | Hanson et al. |
| 7,414,571 | B2 | 8/2008 | Schantz et al. |
| 7,541,942 | B2 | 6/2009 | Cargonja et al. |
| 7,768,393 | B2 | 8/2010 | Nigam |
| 7,937,829 | B2 | 5/2011 | Peterson et al. |
| 7,940,173 | B2 | 5/2011 | Koen |
| 7,944,350 | B2 | 5/2011 | Culpepper et al. |
| 7,956,746 | B2 | 6/2011 | Truscott et al. |
| 8,026,814 | B1 | 9/2011 | Heinze et al. |
| 8,102,271 | B2 | 1/2012 | Heo et al. |
| 8,125,339 | B2 | 2/2012 | Neuwirth |
| 8,193,918 | B1 | 6/2012 | Shavelsky et al. |
| 8,334,773 | B2 | 12/2012 | Cova et al. |
| 8,339,244 | B2 | 12/2012 | Peden, II et al. |
| 8,351,546 | B2 | 1/2013 | Vitek |
| 8,373,562 | B1 | 2/2013 | Heinze et al. |
| 8,384,542 | B1 | 2/2013 | Merrill et al. |
| 8,395,496 | B2 | 3/2013 | Joshi et al. |
| 8,432,274 | B2 | 4/2013 | Cova et al. |
| 8,471,715 | B2 | 6/2013 | Solazzo et al. |
| 8,487,757 | B2 | 7/2013 | Culpepper et al. |
| 8,494,581 | B2 | 7/2013 | Barbosa et al. |
| 8,514,082 | B2 | 8/2013 | Cova et al. |
| 8,515,389 | B2 | 8/2013 | Smetters et al. |
| 8,526,884 | B1 | 9/2013 | Price et al. |
| 8,532,718 | B2 | 9/2013 | Behzad et al. |
| 8,889,944 | B2 | 11/2014 | Abraham et al. |
| 8,962,909 | B2 | 2/2015 | Groosman et al. |
| 2003/0020615 | A1 | 1/2003 | Zand et al. |
| 2003/0036354 | A1 | 2/2003 | Lee et al. |
| 2004/0000571 | A1 | 1/2004 | Reiserer |
| 2005/0052315 | A1 | 3/2005 | Winterling et al. |
| 2005/0115308 | A1 | 6/2005 | Koram et al. |
| 2005/0266808 | A1 * | 12/2005 | Reunamaki ............ H04B 1/005 455/101 |
| 2006/0047480 | A1 | 3/2006 | Lenz et al. |
| 2006/0092031 | A1 | 5/2006 | Vokey et al. |
| 2006/0249401 | A1 | 11/2006 | Lehmann et al. |
| 2007/0046481 | A1 | 3/2007 | Vokey et al. |
| 2007/0211768 | A1 | 9/2007 | Cornwall et al. |
| 2008/0068217 | A1 | 3/2008 | Van Wyk et al. |
| 2008/0300559 | A1 | 12/2008 | Gustafson et al. |
| 2009/0295572 | A1 | 12/2009 | Grim, III et al. |
| 2010/0117836 | A1 * | 5/2010 | Seyed Momen ........ G01S 1/70 340/573.1 |
| 2010/0304091 | A1 | 12/2010 | Wang |
| 2011/0030875 | A1 | 2/2011 | Conte et al. |
| 2011/0077909 | A1 | 3/2011 | Gregory et al. |
| 2011/0128129 | A1 | 6/2011 | Graczyk et al. |
| 2011/0187393 | A1 | 8/2011 | Vokey et al. |
| 2011/0254682 | A1 | 10/2011 | Sigrist Christensen |
| 2012/0161942 | A1 | 6/2012 | Muellner et al. |
| 2013/0041623 | A1 | 2/2013 | Kumar et al. |
| 2013/0072870 | A1 | 3/2013 | Heppe et al. |
| 2013/0150769 | A1 | 6/2013 | Heppe |
| 2013/0274663 | A1 | 10/2013 | Heppe |
| 2014/0026978 | A1 | 1/2014 | Savaria |
| 2014/0290394 | A1 | 10/2014 | Grossman et al. |
| 2015/0002274 | A1 | 1/2015 | Sengstaken, Jr. |
| 2015/0130637 | A1 | 5/2015 | Sengstaken, Jr. |
| 2015/0143881 | A1 | 5/2015 | Raut et al. |
| 2015/0230716 | A1 | 8/2015 | Heppe |
| 2016/0274162 | A1 | 9/2016 | Freeman et al. |

* cited by examiner

WIRELESS HAND HYGIENE TRACKING SYSTEM AND RELATED TECHNIQUES

CROSS-REFERENCE TO RELATED APPLICATIONS

This patent application claims the benefit of U.S. Provisional Patent Application No. 62/337,846, titled "Handwashing Compliance System and Related. Methods," filed on May 17, 2016. Furthermore, this patent application is a Continuation-in-Part of U.S. patent application Ser. No. 14/304,195, titled "Asset Tag Apparatus and Related Methods," filed on Jun. 13, 2014, which claims the benefit of each of: U.S. Provisional Patent Application No. 61/839,561, titled "BlueTooth Asset and Sensor Tag," filed on Jun. 26, 2013; U.S. Provisional Patent Application No. 61/902,316, titled "Bluetooth Asset Tag Signpost," filed on Nov. 11, 2013; U.S. Provisional Patent Application No. 61/902,325, titled "Bluetooth Stockbin Indicator Tag," filed on Nov. 11, 2013; and U.S. Provisional Patent Application No. 61/974,770, titled "Asset Tag Apparatus and Related Methods," filed on Apr. 3, 2014. Furthermore, this patent application is related to U.S. patent application Ser. No. 15/497,530, titled "Wireless Asset Location Tracking System and Related Techniques," filed on Apr. 26, 2017, which is a Continuation-in-Part of U.S. patent application Ser. No. 14/304,195, identified above. Each of these patent applications is herein incorporated by reference in its entirety.

FIELD OF THE DISCLOSURE

The present disclosure relates to hand hygiene compliance tracking and more particularly to a wireless hand hygiene compliance tracking system and related techniques.

BACKGROUND

Hand hygiene is an important aspect of daily life in the fight to prevent or otherwise minimize the spreading of disease. By cleaning one's hands, pathogens, including bacteria and viruses, as well as harmful chemicals and other potentially dangerous substances may be removed, reducing health risks. To this end, soaps, detergents, and alcohol-based hand hygiene agents, such as hand sanitizers, are typically used. Hand hygiene practices are especially important in the administration of medicine and medical care, as well as in preparing and serving food to consumers.

SUMMARY

The subject matter of this application may involve, in some cases, interrelated products, alternative solutions to a particular problem, and/or a plurality of different uses of a single system or article.

One example embodiment provides a wireless hand hygiene compliance tracking system. The system includes a micro-zone transmitter device configured to transmit a first signal including data pertaining to a unique identifier associated with the micro-zone transmitter device and a type of the micro-zone transmitter device, wherein: the type of the micro-zone transmitter device is indicative of whether the micro-zone transmitter device is configured to be deployed at a patient zone, an unsanitary zone, a hand washing station zone, or a hand sanitizing station zone; and the first signal is of a frequency in at least one of a 902 MHz ISM band, a 915 MHz ISM band, an 869 MHz ISM band, an 894 MHz ISM band, and a 433 MHz ISM band. The system further includes a beacon tag device including a wireless receiver configured to receive the first signal including the data pertaining to the unique identifier associated with the micro-zone transmitter device and the type of the micro-zone transmitter device. The beacon tag device further includes a wireless transmitter configured to transmit a second signal of a frequency in an ISM band of between 2.4-2.485 GHz, wherein the second signal includes data pertaining to: a unique identifier associated with the beacon tag device; the unique identifier associated with the micro-zone transmitter device; the type of the micro-zone transmitter device; and either a hand hygiene compliance status or a hand hygiene non-compliance status. The beacon tag further includes a motion detection sensor configured to detect at least one of movement of the beacon tag device and an impact to the beacon tag device and, in response thereto, output a wake-up signal causing the wireless transmitter to transmit the second signal external to the beacon tag device. In some cases, the second signal further includes data pertaining to at least one of: a unique identifier associated with the patient zone at which the micro-zone transmitter device is configured to be deployed; a unique identifier associated with the hand washing station zone at which the micro-zone transmitter device is configured to be deployed; and a unique identifier associated with the hand sanitizing station zone at which the micro-zone transmitter device is configured to be deployed. In some such cases, the second signal further includes data pertaining to at least one of: a status of the beacon tag device; a power level of a power supply of the beacon tag device; and an output of a sensor of the beacon tag device. In some instances, the micro-zone transmitter device: is configured to be deployed at the hand washing station zone; and further includes: a proximity sensor configured to detect a physical presence of an individual tagged with the beacon tag device at the hand washing station zone; and a timer configured to track a time elapsed during detection of the physical presence of the individual tagged with the beacon tag device at the hand washing station zone. In some cases, the micro-zone transmitter device: is configured to be deployed at the hand sanitizing station zone; and further includes a pressure sensor configured to detect activation of a hand sanitizer dispenser by an individual tagged with the beacon tag device at the hand sanitizing station zone. In some instances, the beacon tag device further includes at least one of an audio output device configured to emit a sound; an optical output device configured to emit light; and a vibratory output device configured to emit vibration. Moreover, if the second signal includes data pertaining to the hand hygiene non-compliance status, the beacon tag device is configured to at least one of: emit the sound via the audio output device in a manner indicative of the hand hygiene non-compliance status; emit light via the optical output device in a manner indicative of the hand hygiene non-compliance status; and emit vibration via the vibratory output device in a manner indicative of the hand hygiene non-compliance status. In some cases, the system further includes a gateway configured to communicate with: the micro-zone transmitter device; the beacon tag device; and a server database.

Another example embodiment provides a beacon tag device. The beacon tag device includes a wireless receiver configured to receive a first signal including data pertaining to: a unique identifier associated with a remote source of the first signal; and a type of the remote source of the first signal, wherein the type is indicative of whether the remote source is configured to be deployed at a patient zone, an unsanitary zone, a hand washing station zone, or a hand sanitizing station zone. The beacon tag device further includes a wireless transmitter configured to transmit a second signal of a frequency in an ISM band of between 2.4-2.485 GHz, wherein the second signal includes data pertaining to: a unique identifier associated with the beacon tag device; the unique identifier associated with the remote source of the first signal; the type of the remote source of the first signal; and either a hand hygiene compliance status or a hand hygiene non-compliance status associated with an individual tagged with the beacon tag device. The beacon tag device further includes a processor configured to instruct the wireless transmitter to transmit the second signal. The beacon tag device further includes a motion detection sensor configured to detect at least one of movement of the beacon tag device and an impact to the beacon tag device and, in response thereto, output a wake-up signal to the processor, the wake-up signal causing the processor to transition out of a sleep-state or an off-state, wherein the processor is configured to instruct the wireless transmitter to transmit the second signal in response to receipt of the wake-up signal. In some cases, the first signal is of a frequency in at least one of a 902 MHz ISM band, a 915 MHz ISM band, an 869 MHz ISM band, an 894 MHz ISM band, and a 433 MHz ISM band. In some instances, the second signal further includes data pertaining to at least one of: a unique identifier associated with the patient zone at which the remote source of the first signal is configured to be deployed; a unique identifier associated with the hand washing station zone at which the remote source of the first signal is configured to be deployed; and a unique identifier associated with the hand sanitizing station zone at which the remote source of the first signal is configured to be deployed. In some such instances, the second signal further includes data pertaining to at least one of: a status of the beacon tag device; a power level of a power supply of the beacon tag device; and an output of a sensor of the beacon tag device. In some cases, the beacon tag device further includes at least one of a memory and a processor, wherein the at least one a memory and a processor is configured to have implemented thereat state machine logic utilized in determining the hand hygiene compliance status or the hand hygiene non-compliance status associated with the individual tagged with the beacon tag device. In some such cases, the state machine logic is directed to hand hygiene compliance tracking in at least one of a patient interaction context and a bathroom context. In some instances, the beacon tag device further includes at least one of: an audio output device configured to emit a sound; an optical output device configured to emit light; and a vibratory output device configured to emit vibration. Moreover, if the second signal includes data pertaining to the hand hygiene non-compliance status, the processor is further configured to at least one of: instruct the audio output device to emit the sound in a manner indicative of the hand hygiene non-compliance status; instruct the optical output device to emit light in a manner indicative of the hand hygiene non-compliance status; and instruct the vibratory output device to emit vibration in a manner indicative of the hand hygiene non-compliance status.

Another example embodiment provides a transmitter device. The transmitter device includes a wireless transmitter configured to transmit a first signal including data pertaining to: a unique identifier associated with the transmitter device; and a type of the transmitter device, wherein the type of the transmitter device is indicative of whether the transmitter device is configured to be deployed at a patient zone, an unsanitary zone, a hand washing station zone, or a hand sanitizing station zone. The transmitter device further includes a wireless transceiver configured to receive a second signal from a remote source, wherein the second signal is of a frequency in an ISM band of between 2.4-2.485 GHz. The transmitter device further includes a processor configured to instruct the wireless transmitter to transmit the first signal. In some cases, the first signal is of a frequency in at least one of a 902 MHz ISM band, a 915 MHz ISM band, an 869 MHz ISM band, an 894 MHz ISM band, and a 433 MHz ISM band. In some instances, the first signal includes data that causes a beacon tag device configured to receive the first signal to emit at least one of sound, light, emit vibration in a manner indicative of a hand hygiene non-compliance status associated with an individual tagged with the beacon tag device. In some cases, the transmitter device is configured to be deployed at only one of the patient zone, the unsanitary zone, the hand washing station zone, and the hand sanitizing station zone. In some instances, the transmitter device is programmable to be deployed at any or all of the patient zone, the unsanitary zone, the hand washing station zone, and the hand sanitizing station zone. In some cases, the transmitter device: is configured to be deployed at the hand washing station zone; and further includes: a proximity sensor configured to detect a physical presence of an individual at the hand washing station zone; and a timer configured to track a time elapsed during detection of the physical presence of the individual at the hand washing station zone. In some instances, the transmitter device: is configured to be deployed at the hand sanitizing station zone; and further includes a pressure sensor configured to detect activation of a hand sanitizer dispenser at the hand sanitizing station zone. In some such instances, the transmitter device is configured to be integrated directly with the hand sanitizer dispenser. In some cases, the wireless transmitter is configured with a programmable transmission power.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes and not to limit the scope of the inventive subject matter.

Figure 1:
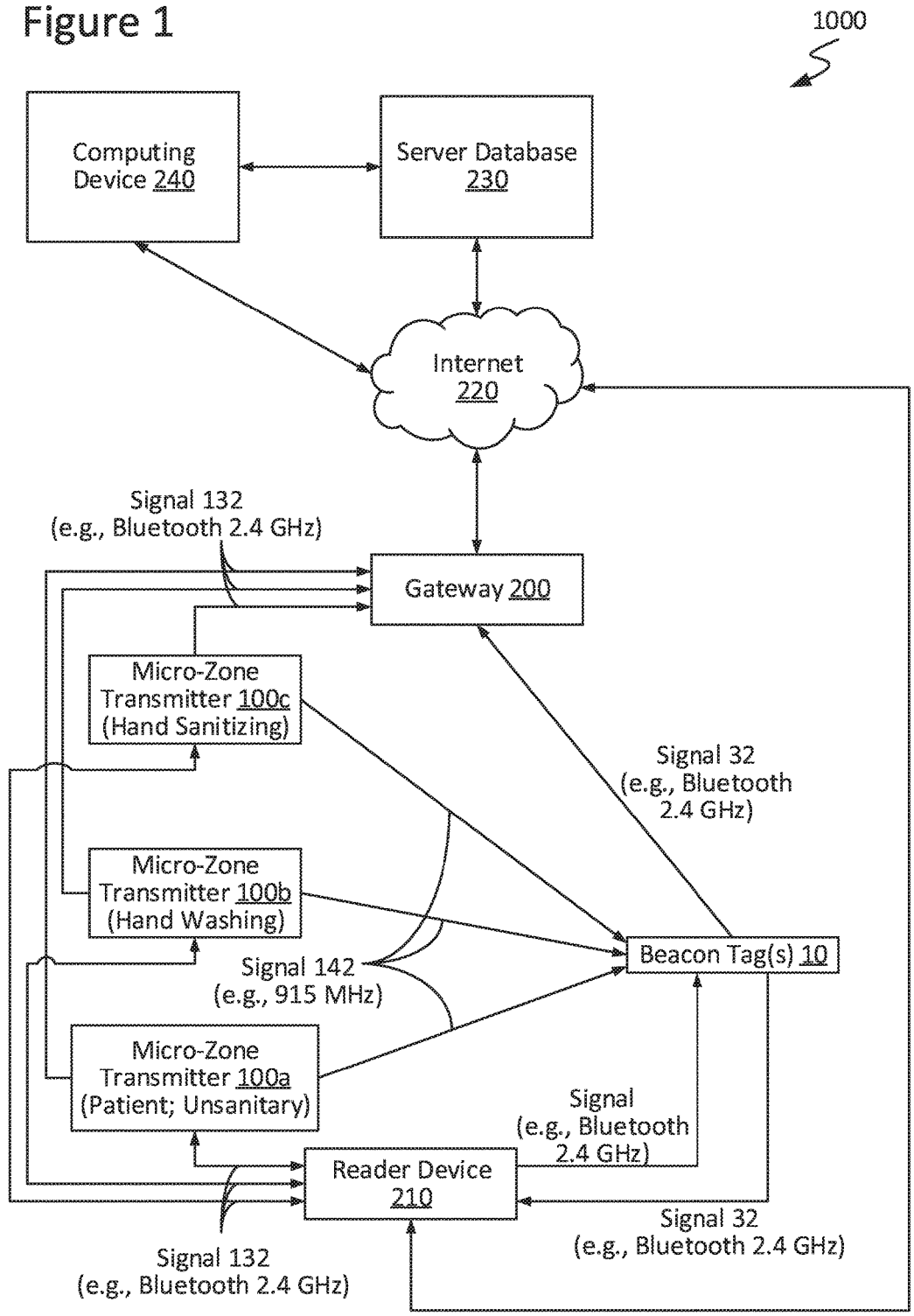
FIG. 1 illustrates a wireless hand hygiene tracking system configured in accordance with an embodiment of the present disclosure.

These and other features of the present embodiments will be understood better by reading the following detailed description, taken together with the figures herein described. In the drawings, each identical or nearly identical component that is illustrated in various figures may be represented by a like numeral. For purposes of clarity, not every component may be labeled in every drawing. Furthermore, as will be appreciated in light of this disclosure, the accompanying drawings are not intended to be drawn to scale or to limit the described embodiments to the specific configurations shown.

DETAILED DESCRIPTION

A wireless hand hygiene compliance tracking system and related techniques are disclosed. The system may include one or more micro-zone (mZone) transmitters configured to be deployed at designated locations where hand hygiene compliance is desired, such as in a patient's room or in a bathroom, to name a few examples. A given mZone transmitter may transmit an mZone signal including data pertaining to its type and identity, from which its purpose and location may be derived. An individual to be monitored may host a beacon tag configured to receive the mZone signal and pull mZone type and identification data therefrom, relaying that data in its own beacon signal, along with other data including a current hand hygiene compliance or non-compliance status. The beacon tag may be programmed with one or more hand hygiene compliance modes, which may be selected based on the desired monitoring context. The beacon signal may be received by any gateway or reader device within transmission range. In this manner, compliant and non-compliant events may be registered by the beacon tag and logged by the server database. When received by a gateway, information from the beacon signal may be delivered through the internet to a server database, which may be cloud-based in some instances, allowing for inter-networking of the system components and other elements as part of the internet of things (IOT). Reader devices and other computing devices may access the information stored at the server database to monitor the hand hygiene compliance history of the tagged individuals, as well as control overall system operation. In some cases, the disclosed system may be configured to provide handwashing compliance metrics on a periodic or other desired basis. In some cases, the disclosed system may be configured to provide a reminder or other immediate feedback to a monitored individual when non-compliant. Numerous configurations and variations will be apparent in light of this disclosure.

General Overview

In hospitals and clinics, as well as food-service industry locales, transmission of pathogens because of insufficient hand hygiene compliance is an ever-present risk, and the cost of resulting infections can be very high, both in terms of patient, personnel, and consumer safety, as well as monetarily. Radio-based hand hygiene compliance monitoring systems are used in various enterprises and facilities to monitor and track individuals' adherence to hand washing and hand sanitization protocols, in effort to provide knowledge of the compliance history of a given tagged individual. With existing approaches, however, installing the infrastructure to enable this monitoring and tracking is normally expensive, and the hand hygiene sensors typically have sufficient power to operate only for a very limited time before their batteries are depleted and the sensors stop working. Moreover, the use of global positioning system (GPS)-based devices with cellular communications is an option that is too expensive for widespread use, due to the high cost of the unit, installation costs, and cellular connection fees, and which does not operate sufficiently indoors. Furthermore, the costs of the infrastructure for many conventional hand hygiene compliance monitoring and tracking systems, including radio-frequency identification (RFID) readers for passive RFID tags, can be prohibitively high to prospective users. Moreover, some existing approaches require individuals to carry or wear additional sensors or to perform additional steps to verify compliance, interfering with day-to-day operating efficiency and negatively impacting productivity.

In addition, the battery life of existing devices is severely limited due to several factors. One factor is that existing devices are location-aware, which means they receive signals from infrastructure that are associated with specific locations, and the tags then must report the location data back to a compliance monitoring and tracking system. These devices also normally use a two-way protocol, which includes sending a message and receiving an acknowledgment of receipt. Having to replace the battery or entirety of these existing devices is an expensive and often time-consuming process. Additionally, it can be difficult to determine the optimal time for replacement of a battery, thereby leaving the user at risk of the tracking device fully losing power and subsequently failing. Some low-power radios have been used to increase battery life, but these devices have shorter transmission range, requiring the RF infrastructure to relay.

Thus, and in accordance with some embodiments of the present disclosure, a wireless hand hygiene compliance tracking system and related techniques are disclosed. The system may include one or more micro-zone (mZone) transmitters configured to be deployed at designated locations where hand hygiene compliance is desired, such as in a patient's room or in a bathroom, to name a few examples. A given mZone transmitter may transmit an mZone signal including data pertaining to its type and identity, from which its purpose and location may be derived. An individual to be monitored may host a beacon tag configured to receive the mZone signal and pull mZone type and identification data therefrom, relaying that data in its own beacon signal, along with other data including a current hand hygiene compliance or non-compliance status. The beacon tag may be programmed with one or more hand hygiene compliance modes, which may be selected based on the desired monitoring context. The beacon signal may be received by any gateway or reader device within transmission range. In this manner, compliant and non-compliant events may be registered by the beacon tag and logged by the server database. When received by a gateway, information from the beacon signal may be delivered through the internet to a server database, which may be cloud-based in some instances, allowing for inter-networking of the system components and other elements as part of the internet of things (IOT). Reader devices and other computing devices may access the information stored at the server database to monitor the hand hygiene compliance history of the tagged individuals, as well as control overall system operation. In some cases, the disclosed system may be configured to provide handwashing compliance metrics on a periodic or other desired basis. In some cases, the disclosed system may be configured to provide a reminder or other immediate feedback to a monitored individual when non-compliant.

In accordance with some embodiments, the disclosed system may be used in tracking hand washing and sanitizing practices in any of a wide range of contexts. For instance, some embodiments may be utilized in tracking compliance in the context of a patient's room at a hospital or clinic, monitoring whether a tagged individual washed or sanitized his hands before interacting with a patient. Some embodiments may be utilized in tracking compliance in the context of a bathroom of a restaurant or other food-service related facility, monitoring whether a tagged individual washed or sanitized his hands before exiting a monitored area and returning to food preparation. If the tagged individual fails to wash or sanitize, the system may log a non-compliant event, and the beacon tag with which the individual is tagged may issue one or more types of feedback to alert the individual of the non-compliant state, in accordance with some embodiments. The present disclosure is not intended to be limited only to these specific example contexts, however, as numerous other suitable uses of the disclosed system and techniques will be apparent in light of this disclosure. For example, some embodiments may be used in tracking individuals in their hand hygiene routines in the context of handling chemical, biological, radiological, nuclear, or other hazardous materials in contexts such as in a laboratory or a manufacturing plant or at a clean-up site, to name a few.

In accordance with some embodiments, the disclosed system may make use of compliance rules, time limits, and other management parameters that provide for a given degree of hand hygiene compliance tracking desired for a given context. In some cases, the various parameters employed in a given hand hygiene compliance mode may be customizable, in accordance with some embodiments. Consequently, the disclosed system may not be prone to false alerts of hand hygiene non-compliance, providing a robust means of tracking hand hygiene.

Moreover, accurate and reliable tracking may be provided via the disclosed system with minimal or otherwise negligible impact on daily processes in patient care, food preparation, or laboratory practices, for example, because the system may accommodate the typical actions and routines of a monitored individual, in accordance with some embodiments. For instance, in some cases, an individual tagged with a beacon tag configured as described herein may be permitted to approach a patient for a short time before being required to wash or sanitize his hands. In some instances, the tagged individual may be permitted to leave the patient and return within a time limit without being required to wash or sanitize his hands again. Contrariwise, in at least some cases, a tagged individual may not be permitted to go from one patient to another or from a designated unsanitary zone to a patient without first washing or sanitizing his hands. Numerous other custom hand hygiene compliance protocols may be implemented using the disclosed system, in part or in whole, as desired for a given target application or end-use. Consequently, the disclosed system may be used to track hand hygiene compliance, as well as provide reminders if not in compliance, in a manner unobtrusive to the tagged individual's normal work flow.

In some cases, an mZone transmitter configured as provided herein may be lower in construction and operation costs than existing WIFI-based options. In some instances, an mZone transmitter configured as provided herein may be amenable to quick and simple installation within a given target space. In some cases, an mZone transmitter configured as provided herein may be battery-operated and thus may be readily relocatable within a given target space. In some instances, use of techniques disclosed herein may provide a hospital, clinic, restaurant, or other facility or locale with accurate hand hygiene compliance information at a fraction of the cost of traditional WIFI-based approaches. As will be appreciated in light of this disclosure, Bluetooth communication is a very energy-efficient wireless communication protocol and by using low-cost batteries, several years of operation from beacon tags and mZone transmitters may be achieved, in accordance with some embodiments. For example, in some cases, the disclosed mZone transmitters can operate from low-cost batteries for over a year, and the disclosed beacon tag receivers can operate for up to about five years on a coin-cell battery. Moreover, in being configured to communicate in various bandwidths that do not interfere with existing Bluetooth and WIFI signal bands, the disclosed system may be utilized without requiring any upgrade to existing information technology infrastructure, at least in some instances.

System Architecture and Operation

FIG. 1 illustrates a wireless hand hygiene tracking system 1000 configured in accordance with an embodiment of the present disclosure. As can be seen, system 1000 may include one or more beacon tags 10, one or more micro-zone (mZone) transmitters 100a, 100b, 100c. For consistency and ease of understanding of the present disclosure, mZone transmitters 100a, 100b, and 100c may be collectively referred to generally as mZone transmitters 100, except where separately referenced. As can be seen further, system 1000 may include a gateway 200 and a server database 230. Moreover, system 1000 may involve in its operation one or more reader devices 210, the internet 220, and a computing device 240. Each of these various dements is discussed in turn below. More generally, FIG. 1 illustrates communicative coupling of the various constituent elements of system 1000 and the overall flow of data within system 1000, in accordance with some embodiments.

Figure 2:
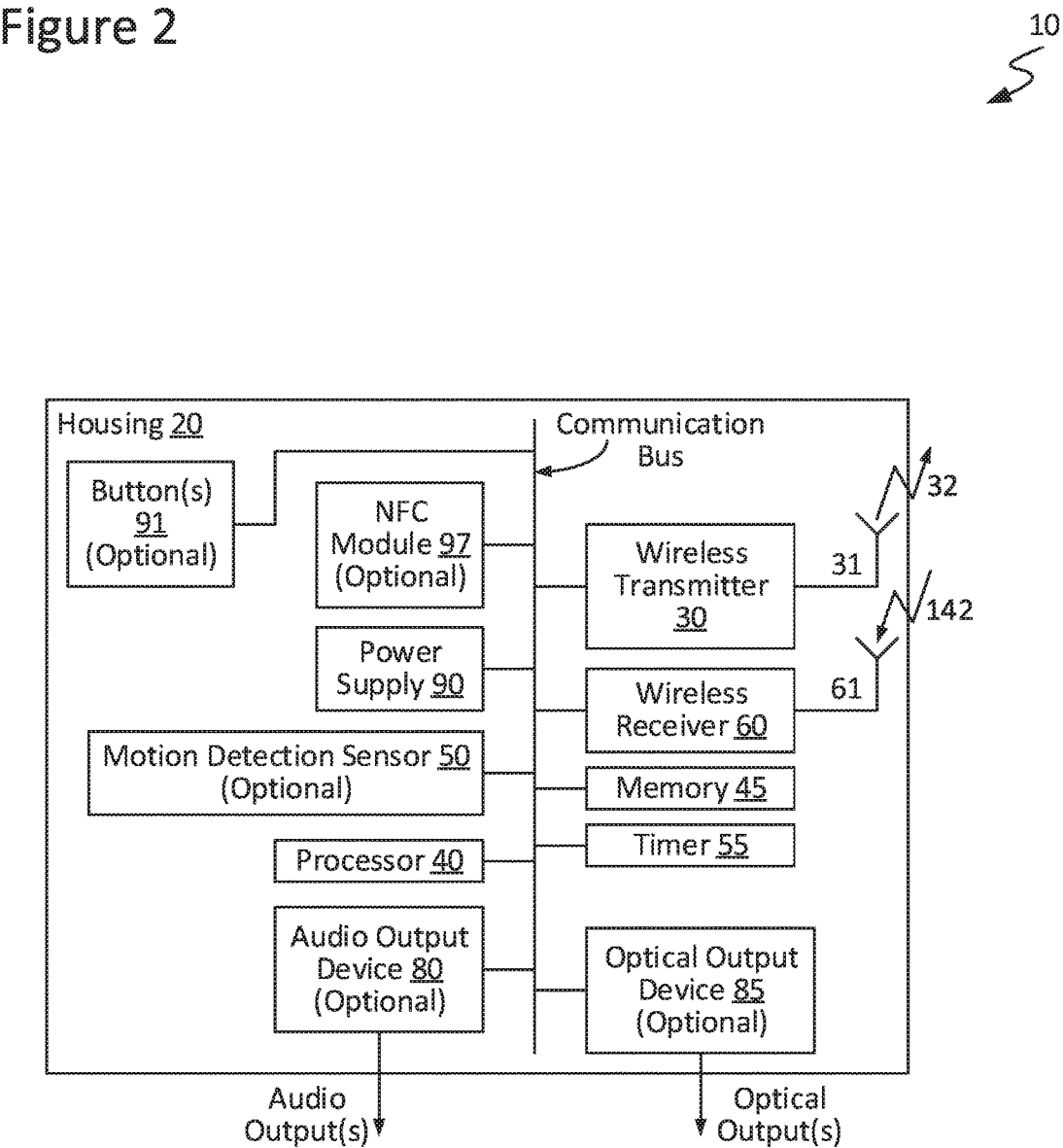
FIG. 2 is a block diagram of a beacon tag configured in accordance with an embodiment of the present disclosure.

A given beacon tag 10 may be configured to be hosted by a monitored individual such that the hand hygiene compliance or non-compliance of that individual may be tracked via system 1000. FIG. 2 is a block diagram of a beacon tag 10 configured in accordance with an embodiment of the present disclosure. As can be seen, beacon tag 10 may include a housing 20 configured to house, in part or in whole, any of the various components of beacon tag 10. The material construction and dimensions of housing 20 may be customized, as desired for a given target application or end-use. In some cases, housing 20 may be substantially flat in profile, thereby minimizing or otherwise reducing the physical obtrusiveness of beacon tag 10 to the tagged individual hosting it. In some embodiments, housing 20 may be configured such that beacon tag 10 may be worn on clothing or equipment, for example, as a badge.

In accordance with some embodiments, housing 20 may be configured to be carried or held by a person. In accordance with some other embodiments, housing 20 may be configured to be mounted to a person's clothing or equipment using any of a wide range of suitable mounting means. For instance, in accordance with some embodiments, beacon tag 10 may be configured for mounting to clothing or equipment via any one, or combination, of mechanical fasteners (e.g., such as clamps, clips, button snaps, and threaded means, to name a few), adhesive materials (e.g., hook-and-loop fasteners), and magnets. In accordance with some embodiments, beacon tag 10 may be configured to be held within a pocket on a piece of clothing or equipment or retained by a tether or lanyard which a person might carry on his or her person. In a more general sense, and in accordance with some embodiments, beacon tag 10 may be hosted by an individual regardless of the material composition of his or her clothing or equipment. Other suitable configurations for housing 20 and any related mounting means will depend on a given application and will be apparent in light of this disclosure.

Beacon tag 10 may include a wireless transmitter 30, which may be either a dedicated transmitter device provided with only transmitting capabilities or a transceiver device provided with both transmitting and receiving capabilities. In accordance with some embodiments, wireless transmitter 30 may be a short-wavelength ultra-high frequency (UHF) radio wave Bluetooth-compatible device configured to transmit and/or receive signals of a frequency in an ISM band of between 2.4-2.485 GHz. In some instances in which wireless transmitter 30 is a transceiver device, it may receive signal(s) from an external source, such as a reader device 210 (discussed below), for example, when configuring beacon tag 10. As a wireless communication device, wireless transmitter 30 may include an antenna 31 configured to transmit and/or receive one or more signals, such as a beacon signal 32 (discussed below). To that end, antenna 31 may be, for example, a printed circuit board (PCB) antenna configured as typically done or any other suitable antenna, as will be apparent in light of this disclosure. In accordance with some embodiments, wireless transmitter 30 may be configured to transmit periodically, as desired for a given target application or end-use. In some embodiments, wireless transmitter 30 may be configured to transmit beacon signal 32 from beacon tag 10 at a repetition rate of at least three transmissions per second, though greater or lesser transmission rates may be provided, in accordance with other embodiments. Moreover, the transmission power may be varied, as desired for a given target application or end-use. Other suitable configurations for wireless transmitter 30 and its antenna 31 will depend on a given application and will be apparent in light of this disclosure.

Beacon tag 10 also may include a wireless receiver 60, which may be either a dedicated receiver device provided with only receiving capabilities or a transceiver device provided with both receiving and transmitting capabilities. In accordance with some embodiments, wireless receiver 60 may be a radio-wave wireless receiver device configured to receive and/or transmit signals of a frequency in any one, or combination, of ISM bands, including 902 MHz, 915 894 MHz, 869 MHz, and 433 MHz. As a wireless communication device, wireless receiver 60 may include an antenna 61 configured to receive and/or transmit one or more signals, such as an mZone signal 142 transmitted by a given mZone transmitter 100 (discussed below). To that end, antenna 61 may be, for example, a PCB antenna configured as typically done or any other suitable antenna, as will be apparent in light of this disclosure. In some embodiments, wireless receiver 60 may be, for example, a very low-duty-cycle device, which may help to conserve the power of power supply 90 (discussed below), at least in some instances. In some embodiments, for within a one-second period, wireless receiver 60 may be turned on and able to receive for a first period of about 1 ms or less and turned off and unable to receive for a second period of about 100 ms or less, thereby conserving power. In accordance with some embodiments, wireless receiver 60 may periodically listen for an incoming data packet (e.g., in a given mZone signal 142, discussed below) and, upon reception of a valid data packet, send a wake-up signal to processor 40 (discussed below). Other suitable configurations for wireless receiver 60 and its antenna 61 will depend on a given application and will be apparent in light of this disclosure.

Beacon tag 10 further may include memory 45, which may be implemented with any one, or combination, of volatile and non-volatile memory and may be of any type and size, as desired for a given target application or end-use. In some cases, memory 45 may be configured for use in storing data, on a temporary or permanent basis, whether that data is native to beacon tag 10 or received from another source (e.g., such as a given mZone transmitter 100). In some instances, memory 45 may be configured for use as processor workspace for processor 40 (discussed below). In some embodiments, memory 45 may be used to keep a status count and details of hand hygiene compliant and non-compliant events.

In accordance with some embodiments, memory 45 include, for example, a computer-readable medium that, when executed by a processor (e.g., such as processor 40), carries out any one or more of the functions described herein, in part or in whole. The computer-readable medium may be, for example, a hard drive, a compact disk, a memory stick, a server, or any other suitable non-transitory computer or computing device memory that includes executable instructions, or a plurality or combination of such memories. Other embodiments can be implemented, for instance, with gate-level logic or an application-specific integrated circuit (ASIC) or chip set, or other such purpose-built logic. Some embodiments can be implemented with a microcontroller having input/output (I/O) capability (e.g., inputs for receiving user inputs; outputs for directing other components) and one or more embedded routines for carrying out device functionality. In a more general sense, memory 45 may be implemented in hardware, software, firmware, or a combination thereof, as desired for a given target application or end-use. Other suitable configurations for memory 45 will depend on a given application and will be apparent in light of this disclosure.

In addition, beacon tag 10 may include a processor 40, which may be configured to communicate with any one, or combination, of the other various components of beacon tag 10 via a communication bus or other suitable interconnect. Processor 40 may be, for example, a central processing unit (CPU), a microcontroller unit (MCU), or any other suitable processing element, as will be apparent in light of this disclosure. In performing a given operation associated with beacon tag 10, processor 40 may be configured to access data stored at memory 45 or otherwise accessible to beacon tag 10. When wireless receiver 60 receives a valid mZone signal 142 from a given mZone transmitter 100 (as discussed below), processor 40 may be alerted and may process the data received via that mZone signal 142, in accordance with some embodiments. In accordance with some embodiments, processor 40 may be configured to process, in part or in whole, any of the various state machine logic 600, 700 (discussed below) states. Moreover, processor 40 may be used in transitioning between such states. Other suitable configurations for processor 40 will depend on a given application and will be apparent in light of this disclosure.

Beacon tag 10 may include a timer 55 configured, in accordance with some embodiments, to control periodic transmissions of beacon signal 32 using processor 40. To that end, timer 55 may be configured to output a wake-up signal to processor 40 at a given repetition rate (e.g., one transmission per ten seconds), which may be customized, as desired for a given target application or end-use. In response to receipt of the wake-up signal from timer 55, processor 40 may send another wake-up signal to wireless transmitter 30 and instruct it to transmit beacon signal 32. Also, as described in further detail below, timer 55 may be configured, in accordance with some embodiments, to transition the current state of beacon tag 10 via timeout(s) of a given duration, which may be customized as desired for a given target application or end-use. To that end, timer 55 may be configured, in accordance with some embodiments, for use in tracking the time elapsed in consideration of any of the various time limits and windows utilized in the state machine logic described herein. Timer 55 may be implemented in hardware, software, firmware, or some combination thereof. In some embodiments, timer 55 may be integrated with processor 40. Other suitable configurations for timer 55 will depend on a given application and will be apparent in light of this disclosure.

Beacon tag 10 also optionally may include a motion detection sensor 50, which may be a micro-electromechanical system (MEMS) accelerometer device or any other suitable motion detection device, as will be apparent in light of this disclosure. In accordance with some embodiments, motion detection sensor 50 may be configured to detect movement (e.g., translational movement, rotational movement, and so on) of beacon tag 10 or an impact to beacon tag 10 (e.g., such as a single-tap or double-tap on housing 20). Motion detection sensor 50 may be configured, in accordance with some embodiments, to output a wake-up signal to processor 40 in response to its activation as caused by the movement or impact. In response to receipt of this wake-up signal, processor 40 may transition out of a low-power state (e.g., a sleep-state or an off-state) and instruct wireless transmitter 30 to transmit a beacon signal 32 (discussed below) externally from housing 20. Motion detection sensor 50 also may be configured, in accordance with some embodiments, to output a wake-up signal to wireless receiver 60 in response to its activation as caused by the movement or impact. In this manner, wireless receiver 60 may remain in a low-power state (e.g., a sleep-state or off-state) until beacon tag 10 is moved or impacted, at least in some embodiments. In some instances, motion detection sensor 50 may be a low-power device configured to use about 10 µAh or less, for example, of power provided by power supply 90 (discussed below), though other power consumption ratings may be provided in other embodiments. Other suitable configurations for optional motion detection sensor 50 will depend on a given application and will be apparent in light of this disclosure.

Beacon tag 10 may include a power supply 90, which may be configured to supply a given target amount of power to any of the various components of beacon tag 10. In some embodiments, power supply 90 may be a battery, which may be permanent or replaceable. In some cases, power supply 90 may include or be operatively coupled with a photovoltaic module (e.g., a solar cell) configured to convert light energy to electrical energy for use by beacon tag 10. In accordance with some embodiments, processor 40 may be configured to check the power level of power supply 90 periodically or as otherwise desired. Other suitable configurations for power supply 90 will depend on a given application and will be apparent in light of this disclosure.

In some embodiments, beacon tag 10 optionally may include an audio output device 80, which may be a speaker, beeper, or any other device capable of emitting sound of a given frequency, optionally with a given emission period or pattern. In accordance with some embodiments, audio output device 80 may be configured to output audio output signal(s) indicative of a given condition with respect to the operation of beacon tag 10 (or system 1000 more generally). For instance, in some cases, audio output device 80 may emit a sound indicative of a low power level of power supply 90. In some cases, audio output device 80 may emit a sound indicative of a hand hygiene non-compliance status (discussed below). Other suitable configurations and uses for optional audio output device 80 will depend on a given application and will be apparent in light of this disclosure.

In some embodiments, beacon tag 10 optionally may include one or more optical output devices 85, which may be a solid-state light source, such as a light-emitting diode (LED), or any other device capable of emitting light of a given wavelength, optionally with a given emission period or pattern. In an example case, beacon tag 10 may include a first optical output device 85 configured to emit light of a first wavelength (e.g., green light) and a second optical output device 85 configured to emit light of a different second wavelength (e.g., red light). In accordance with some embodiments, a given optical output device 85 may be configured to output optical output signal(s) indicative of a given condition with respect to the operation of beacon tag 10 (or system 1000 more generally). For instance, in some cases, a given optical output device 85 may be configured to emit light indicative of any one, or combination, of the same various example conditions discussed above with respect to audio output device 80. Other suitable configurations and uses for optional optical output device(s) 85 will depend on a given application and will be apparent in light of this disclosure.

In some embodiments, beacon tag 10 optionally may include a near-field communication (NFC) module 97, which may be configured to transmit and/or receive one or more NFC signals, as typically done. In accordance with some embodiments, NFC module 97 may be utilized, for example, in conjunction with a given contact reader external to beacon tag 10 (e.g., such as at reader device 210, discussed below). Other suitable configurations for optional NFC module 97 will depend on a given application and will be apparent in light of this disclosure.

In some embodiments, beacon tag 10 optionally may include one or more buttons 91, which may be programmable and either a physical control feature (e.g., a physical button, switch, knob, pressure sensor, toggle, slider, and so forth) or a virtual control feature (e.g., a touch-sensitive icon or other element providing any one or more of the aforementioned physical control feature functionalities). In an example case, beacon tag 10 may include a button 91 that, when pressed, causes beacon tag 10 to emit a beacon signal 32. In another example case, beacon tag 10 may include a button 91 that, when pressed, causes beacon tag 10 to enter into a programming mode by which the settings and operation of beacon tag 10 may be customized. In another example case, beacon tag 10 may include a button 91 that, when pressed, causes beacon tag 10 to perform a power level check for power supply 90. Other suitable configurations and functions for button(s) 91 will depend on a given application and will be apparent in light of this disclosure.

It should be noted that beacon tag 10 is not intended to be limited only to the various example sensors and devices discussed above. In accordance with some other embodiments, beacon tag 10 may include any of a wide range of additional (or alternative) sensors, such as any one, or combination, of a temperature sensor, a moisture sensor, a humidity sensor, a proximity sensor, a magnetic field sensor, a chemical sensor, a radiation sensor, and a biological agent sensor, among others. In accordance with some other embodiments, beacon tag 10 may include a haptic feedback or other vibratory output device configured to vibrate in a manner indicative of a given condition with respect to the operation of beacon tag 10 (or system 1000 more generally). In accordance with some other embodiments, beacon tag 10 may include a timer configured to provide a wake-up signal to processor 40, and processor 40 in turn may instruct wireless transmitter 30 to transmit beacon signal 32. In accordance with some embodiments, beacon tag 10 may include a radio-frequency identification (RFID) module configured to communicate with processor 40 and at least one of transmit and receive one or more RFD signals, as typically done. Numerous configurations and variations will be apparent in light of this disclosure.

Figure 3A:
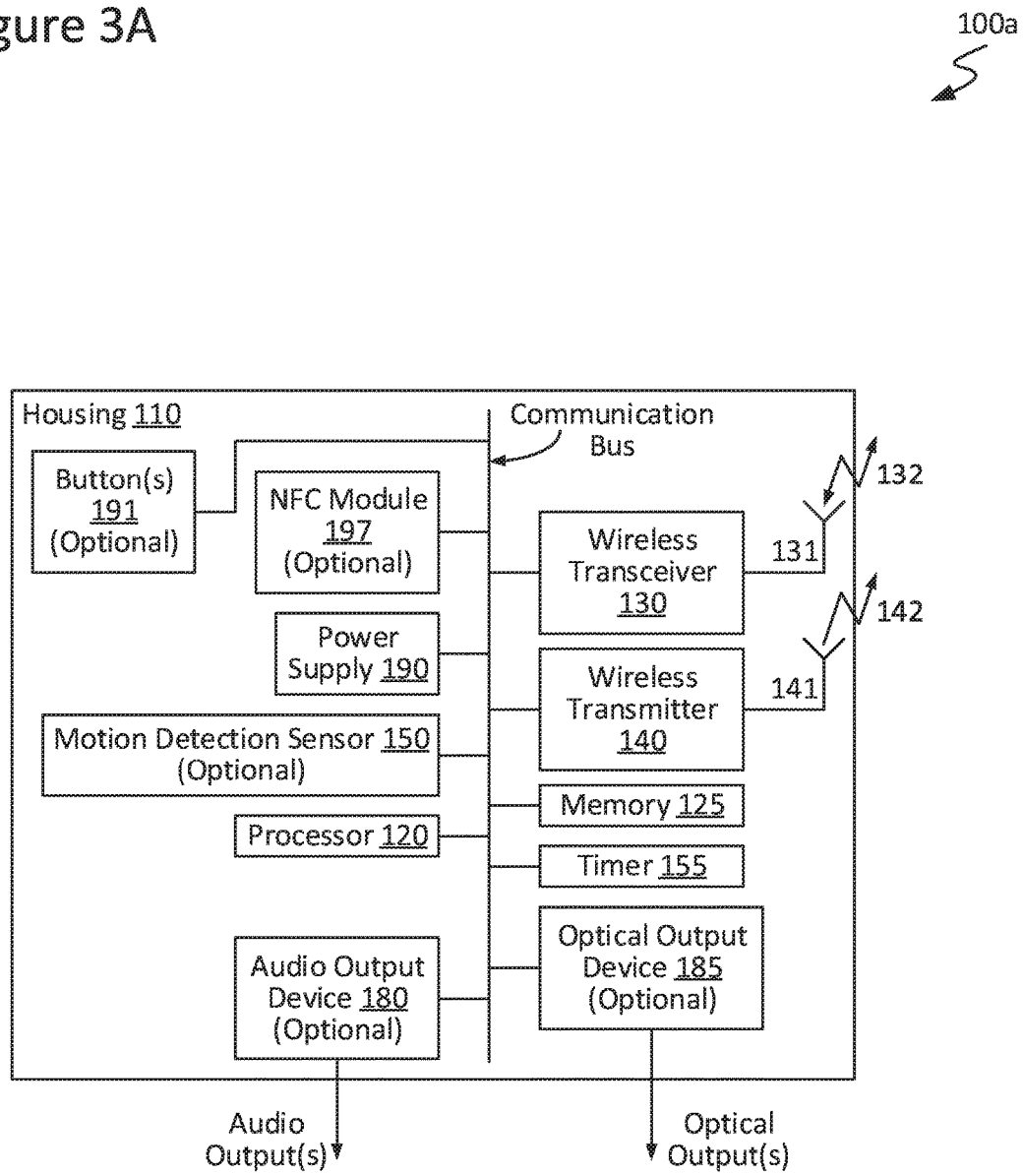
FIG. 3A is a block diagram of a micro-zone (mZone) transmitter configured in accordance with an embodiment of the present disclosure.
Figure 3B:
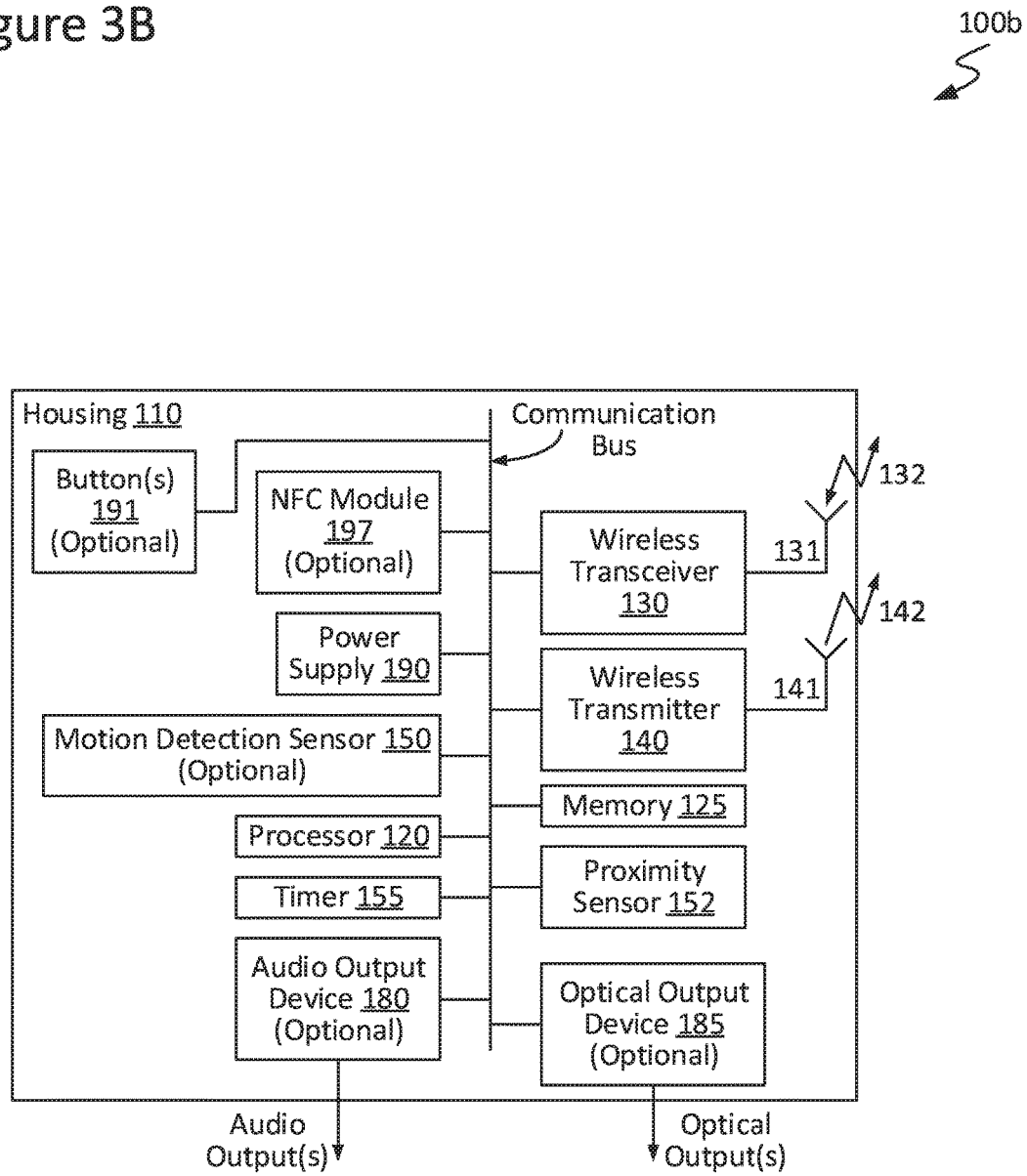
FIG. 3B is a block diagram of an mZone transmitter configured in accordance with another embodiment of the present disclosure.
Figure 3C:
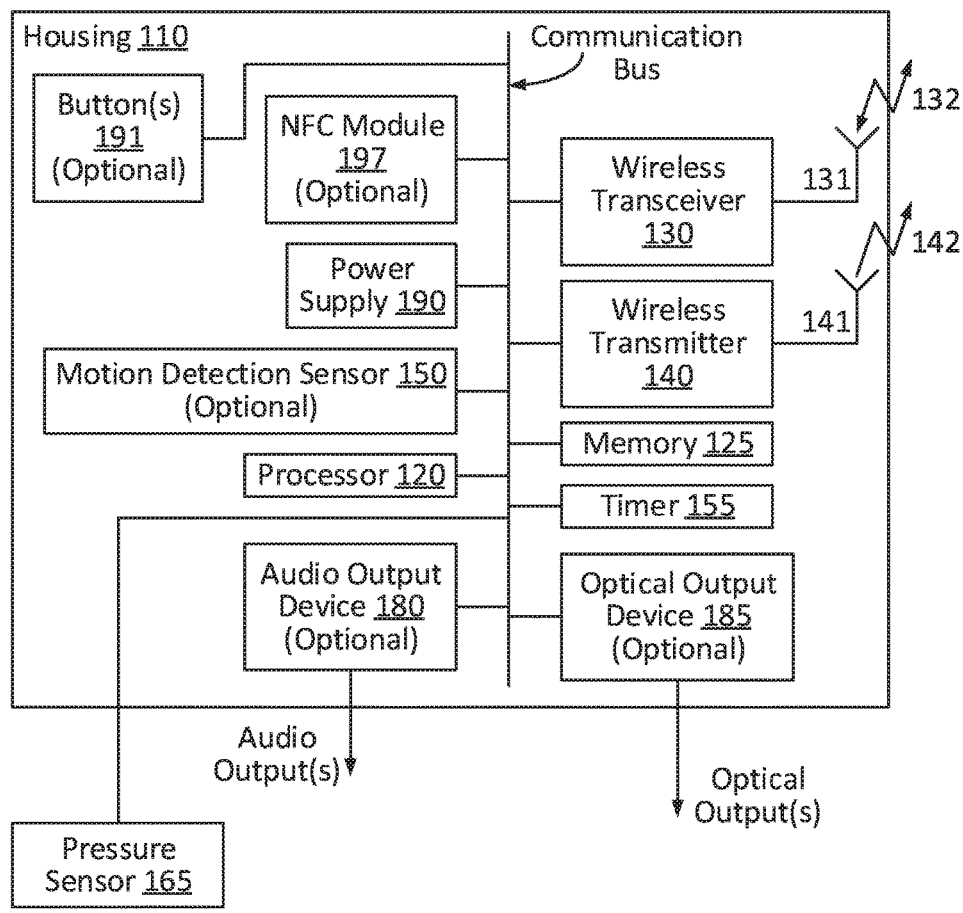
FIG. 3C is a block diagram of an mZone transmitter configured in accordance with another embodiment of the present disclosure.

Returning to FIG. 1, system 1000 may include one or more mZone transmitters 100. FIG. 3A is a block diagram of an mZone transmitter 100a configured in accordance with an embodiment of the present disclosure. FIG. 3B is a block diagram of an mZone transmitter 100b configured in accordance with an embodiment of the present disclosure. FIG. 3C is a block diagram of an mZone transmitter 100c configured in accordance with an embodiment of the present disclosure. As previously noted, unless separately identified, mZone transmitters 100a, 100b, and 100c may be referred to collectively as mZone transmitter(s) 100.

As can be seen from these figures, a given mZone transmitter 100 may include a housing 110 configured to house, in part or in whole, any of the various components of mZone transmitter 100. The material construction and dimensions of housing 110 may be customized, as desired for a given target application or end-use. Other suitable configurations for housing 110 will depend on a given application and will be apparent in light of this disclosure.

A given mZone transmitter 100 may include a wireless transceiver 130, which may be a dedicated transceiver device provided with both transmitting and receiving capabilities. In accordance with some embodiments, wireless transceiver 130 may be a Bluetooth-compatible device configured to transmit and/or receive signals of a frequency in an ISM band of between 2.4-2.485 GHz. In some embodiments, wireless transceiver 130 may be configured to receive signal(s) 132 from an external source, such as a reader device 210 (discussed below) which include instructions that change the operation of mZone transmitter 100. In some instances, wireless transceiver 130 may be configured to receive signal(s) 132 from an external source, such as a reader device 210, when configuring the settings of mZone transmitter 100. Similarly, in some instances, beacon tag 10 may be configured to receive signals from an external source, such as a reader device 210, when configuring the setting of beacon tag 10. In accordance with some embodiments, mZone transmitter 100 may be configured to transmit a beacon signal 132, which may be of a frequency in an ISM band of between 2.4-2.485 GHz. Beacon signal 132 may include data, for example, pertaining to the status of that source mZone transmitter 100, such as a current power level of its power supply 190 (discussed below). As a wireless communication device, wireless transceiver 130 may include an antenna 131 configured to transmit and/or receive one or more signals, such as a signal 132 (discussed below). To such ends, antenna 131 may be, for example, a PCB antenna configured as typically done or any other suitable antenna, as will be apparent in light of this disclosure. Other suitable configurations for wireless transceiver 130 and its antenna 131 will depend on a given application and will be apparent in light of this disclosure.

A given mZone transmitter 100 also may include a wireless transmitter 140, which may be either a dedicated transmitter device provided with only transmitting capabilities or a transceiver device provided with both transmitting and receiving capabilities. In some cases, wireless transmitter 140 may be, for example, a wireless transmitter device configured to receive and/or transmit signals of a frequency in any one, or combination, of ISM bands, including 915 MHz, 902 MHz, 894 MHz, 869 MHz, and 433 MHz. As a wireless communication device, wireless transmitter 140 may include an antenna 141 configured to receive and/or transmit one or more signals, such as an mZone signal 142 (discussed below). To that end, antenna 141 may be, for example, a PCB antenna configured as typically done or any other suitable antenna, as will be apparent in light of this disclosure. In some embodiments, antenna 141 may be omni-directional, directional, or both. In directional cases, antenna 141 also may be circularly polarized, which may help to ensure that a beacon tag 10 within transmission range is more likely to receive mZone signal 142 regardless of the current orientation of that beacon tag 10 on the host tagged individual. In cases where both capabilities are provided, selection may be made, for example, based on the location that is to host mZone transmitter 100. For instance, if a given mZone transmitter 100 is to be mounted on a ceiling in a multi-floor building, then antenna 141 may transmit in a directional manner to help ensure that RF energy of mZone signal 142 is pointed into the desired target area and does not interfere with wireless communications that may be occurring on neighboring floors. If instead a given mZone transmitter 100 is to be disposed outdoors, then antenna 141 may be omni-directional to help ensure that mZone signal 142 has the broadest coverage area in the target space.

In accordance with some embodiments, wireless transmitter 140 may be configured such that its transmission range is programmable via processor 120 (discussed below). In some cases, wireless transmitter 140 may have a transmission range in the range of about 1-30 ft. (e.g., about 1-10 ft., about 10-20 ft., about 20-30 ft., or any other sub-range in the range of about 1-30 ft.). Of course, lesser or greater transmission ranges for wireless transmitter 140 may be provided in accordance with other embodiments, as desired for a given target application or end-use. In a more general sense, wireless transmitter 140 may be programmed to control the transmission power and thus range of transmission from several feet to several hundreds of feet. Moreover, by controlling the transmission power of their wireless transmitters 140, mZone transmitters 100 can be placed in relative proximity to each other. For instance, in some cases, mZone transmitters 100 may be spaced apart from one another by about 6 ft. or less. In this manner, system 1000 may be configured to provide coarse or fine-grained location tracking, as desired for a given target application or end-use. If a beacon tag 10 receives more than one mZone signal 142, then it may use the relative signal strength of the received plurality of mZone signals 142 to determine which source mZone transmitter 100 is closest, helping to determine its location.

In accordance with some embodiments, wireless transmitter 140 may be configured to transmit periodically, as desired for a given target application or end-use. For instance, wireless transmitter 140 may transmit for about 100 MS or more and turn off for about 1-2 s, thereby conserving power, and this cycle may be repeated as desired. As will be appreciated in light of this disclosure, this duration of transmission may help to ensure that the wireless receiver 60 of a given beacon tag 10 receives the transmitted mZone signal 142. As will be further appreciated, this relatively long off-time also may help to ensure that two different mZone transmitters 100 do not interfere with one another in cases where their transmission ranges overlap. Other suitable configurations for wireless transmitter 140 and its antenna 141 will depend on a given application and will be apparent in light of this disclosure.

A given mZone, transmitter 100 further may include memory 125, which may be of any of the various example types, sizes, and configurations discussed above, for instance, with respect to memory 45, in accordance with some embodiments. In some cases, memory 125 may be configured for use in storing data, on a temporary or permanent basis, whether that data is native to a given mZone transmitter 100 or received from another source (e.g., such as a reader device 210). In some instances, memory 125 may be configured for use as processor workspace for processor 120 (discussed below). Other suitable configurations for memory 125 will depend on a given application and will be apparent in light of this disclosure.

In addition, a given mZone transmitter 100 may include a processor 120, which may be configured to communicate with any one, or combination, of the other various components of mZone transmitter 100 via a communication bus or other suitable interconnect. Processor 120 may be, for example, a CPU, an MCU, or any other suitable processing element, as will be apparent in light of this disclosure. In performing a given operation associated with mZone transmitter 100, processor 120 may be configured to access data stored at memory 125 or otherwise accessible to mZone transmitter 100. In accordance with some embodiments, processor 120 may output a control signal to wireless transmitter 140 causing it to transmit periodic data packets in an mZone signal 142 at a programmable transmission strength and transmission range. Other suitable configurations for processor 120 will depend on a given application and will be apparent in light of this disclosure.

MZone transmitter 100 may include a timer 155 configured, in accordance with some embodiments, to control periodic transmissions of mZone signal 42 using processor 120. To that end, timer 155 may be configured to output a wake-up signal to processor 120 at a given repetition rate (e.g., one transmission per ten seconds), which may be customized, as desired for a given target application or end-use. In response to receipt of the wake-up signal from timer 155, processor 120 may send another wake-up signal to wireless transmitter 140 and instruct it to transmit mZone signal 142. Also, as described in further detail below, timer 155 may be configured, in accordance with some embodiments, to permit wireless transmitter 140 to transmit an mZone signal 142 that results in a recipient beacon tag 10 transitioning the current state via timeout(s) of a given duration, which may be customized as desired for a given target application or end-use. To that end, timer 155 may be configured, in accordance with some embodiments, for use in tracking the time elapsed in consideration of any of the various time limits and windows utilized in the state machine logic described herein. Timer 155 may be implemented in hardware, software, firmware, or some combination thereof. In some embodiments, timer 155 may be integrated with processor 120. Other suitable configurations for timer 155 will depend on a given application and will be apparent in light of this disclosure.

A given mZone transmitter 100 also optionally may include a motion detection sensor 150, which may be of any of the various example configurations discussed above, for instance, with respect to motion detection sensor 50, in accordance with some embodiments. Motion detection sensor 150 may be configured, in accordance with some embodiments, to detect movement of a given mZone transmitter 100, which may be indicative of removal thereof from its designated location. Other suitable configurations for optional motion detection sensor 150 will depend on a given application and will be apparent in light of this disclosure.

A given mZone transmitter 100 may include a power supply 190, which may be configured to supply a given target amount of power to any of the various components of mZone transmitter 100. In some embodiments, power supply 190 may be a battery, which may be permanent or replaceable. In an example case, power supply 190 may be a battery configured to power mZone transmitter 100 for a year or more without need of replacement. In some embodiments, power supply 190 may be an AC power supply (with appropriate DC power conversion capabilities). In some embodiments, power supply 190 may include or be operatively coupled with a photovoltaic module (e.g., a solar cell) configured to convert light energy to electrical energy for use by mZone transmitter 100. Other suitable configurations for power supply 190 will depend on a given application and will be apparent in light of this disclosure.

In some embodiments, a given mZone transmitter 100 optionally may include an audio output device 180, which may be of any of the example configurations discussed above, for instance, with respect to audio output device 80. In accordance with some embodiments, optional audio output device 180 may be configured to output audio output signal(s) indicative of a given condition with respect to the operation of mZone transmitter 100 (or system 1000 more generally). For instance, in some cases, audio output device 180 may emit a sound indicative of a low power level of power supply 190. In some cases, audio output device 180 may emit a sound indicative of movement of mZone transmitter 100 from its designated location, as detected by motion detection sensor 150. Other suitable configurations and uses for optional audio output device 180 will depend on a given application and will be apparent in light of this disclosure.

In some embodiments, a given mZone transmitter 100 optionally may include one or more optical output devices 185, which may be of any of the example configurations discussed above, for instance, with respect to optical output device 85. In accordance with some embodiments, a given optical output device 185 may be configured to output optical output signal(s) indicative of a given condition with respect to the operation of mZone transmitter 100 (or system 1000 more generally). For instance, in some cases, a given optical output device 185 may be configured to emit light indicative of any one, or combination, of the same various example conditions discussed above with respect to audio output device 180. Other suitable configurations for optional optical output device(s) 185 will depend on a given application and will be apparent in light of this disclosure.

In some embodiments, a given mZone transmitter 100 optionally may include one or more buttons 191, which may be programmable and of any of the various example physical and virtual configurations discussed above with respect to button(s) 91. In an example case, a given mZone transmitter 100 may include a button 191 that, when pressed, causes that mZone transmitter 100 to emit an mZone signal 142. In another example case, a given mZone transmitter 100 may include a button 191 that, when pressed, causes that mZone, transmitter 100 to enter into a programming mode by which the settings and operation of that mZone transmitter 100 may be customized. In another example case, a given mZone transmitter 100 may include a button 191 that, when pressed, causes that mZone transmitter 100 to perform a power level check for power supply 190. Other suitable configurations and functions for button(s) 191 will depend on a given application and will be apparent in light of this disclosure.

As can be seen in FIG. 3B specifically, mZone transmitter 100b may include a proximity sensor 152, which may be configured to detect the presence of a nearby individual, tagged with a beacon tag 10 or otherwise, in accordance with some embodiments. To this end, proximity sensor 152 may include infrared (IR) transmitter and receiver (e.g., transceiver) componentry. For instance, in an example case, proximity sensor 152 may include: (1) an IR transmitter diode configured to emit an IR signal; and (2) an IR detector to detect the IR signal reflected back by an individual proximate mZone transmitter 100b. In some embodiments, proximity sensor 152 may be internal to or otherwise hosted by housing 110, though this is not required, as in some other embodiments, proximity sensor 152 may be a separate component external to housing 110 and operatively coupled with the communication bus of mZone transmitter 100b. Timer 155 may be configured, in accordance with some embodiments, to track the elapsed time pertaining to detection of the tagged individual by proximity sensor 152. Other suitable configurations for proximity sensor 152 will depend on a given application and will be apparent in light of this disclosure.

As can be seen in FIG. 3C specifically, mZone transmitter 100c may include a pressure sensor 165, which may be configured to detect operation of hand sanitizer dispenser 300, 350 (discussed below). To this end, pressure sensor 165 may include resistive change sensor componentry configured such that, when pressure is applied to pressure sensor 165 in dispensing hand sanitizer, a change in resistance is detected by processor 120. In some embodiments, pressure sensor 165 may be external to housing 110 and operatively coupled with the communication bus of mZone transmitter 100c, though this is not required, as in some other embodiments, pressure sensor 165 may be internal to or otherwise hosted by housing 110. Output of pressure sensor 165 may be processed by processor 120 or by some other dedicated processing element. In some embodiments, analog-to-digital converter (ADC) componentry may be utilized in monitoring pressure sensor 165 and relaying input to processor 120. In some cases, pressure sensor 165 optionally may be configured to detect the fill level (e.g., based on detected weight) of the hand sanitizer dispenser 300, 350 hosting mZone transmitter 100c. Other suitable configurations for pressure sensor 165 will depend on a given application and will be apparent in light of this disclosure.

It should be noted that beacon tags 10 and mZone transmitters 100 are not intended to be limited only to the example configurations described above and illustrated in FIGS. 2 and 3A-3C, as numerous other configurations and variations will be apparent in light of this disclosure. For instance, in some other embodiments, any (or all) of memory 45, processor 40, wireless transmitter 30, and wireless receiver 60 may be provided as a single device having the capabilities of each attendant component. Similarly, in some embodiments, any (or all) of memory 125, processor 120, wireless transceiver 130, and wireless transmitter 140 may be provided as a single device having the capabilities of each attendant component.

In accordance with some embodiments, an mZone transmitter 100c may be operatively coupled with a given hand sanitizer station, whether of a dispenser unit form or a pump bottle form. As will be appreciated in light of this disclosure, the hand sanitizer station may be manually or electronically operable to dispense hand sanitizer.

Figure 4A:
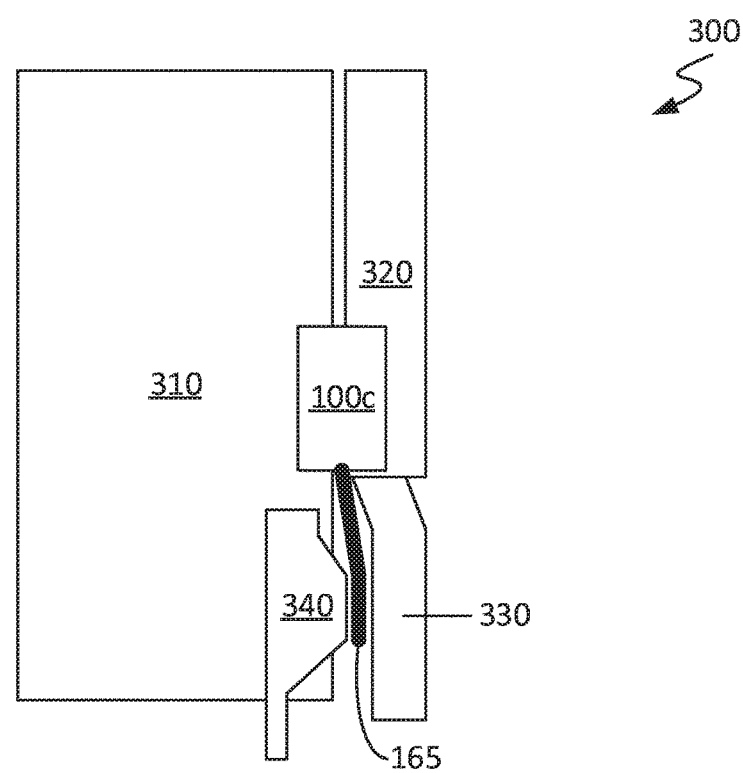
FIG. 4A is a cross-sectional side elevation view of a mountable hand sanitizer dispenser unit including an mZone transmitter configured in accordance with an embodiment of the present disclosure.

FIG. 4A is a cross-sectional side elevation view of a mountable hand sanitizer dispenser unit 300 including an mZone transmitter 100c configured in accordance with an embodiment of the present disclosure. As can be seen, mZone transmitter 100c may be disposed within body portion 310 and protected by faceplate portion 320 such that pressure sensor 165 extends beside actuator portion 330. Activation (e.g., pressing via the hand) of actuator portion 330 to dispense hand sanitizer from nozzle portion 340 may impart sufficient pressure on pressure sensor 165 to register dispensation, and that data may be used in recording a hand hygiene compliance event. In response to dispensing the hand sanitizer, mZone transmitter 100c may transmit an mZone signal 142 including data pertaining to the compliance event, which may be received by a beacon tag 10 within transmission range. As will be appreciated in light of this disclosure, mountable hand sanitizer dispenser unit 300 may be configured to be affixed, in a temporary or permanent manner, to any surface or structure, as desired for a given target application or end-use.

Figure 4B:
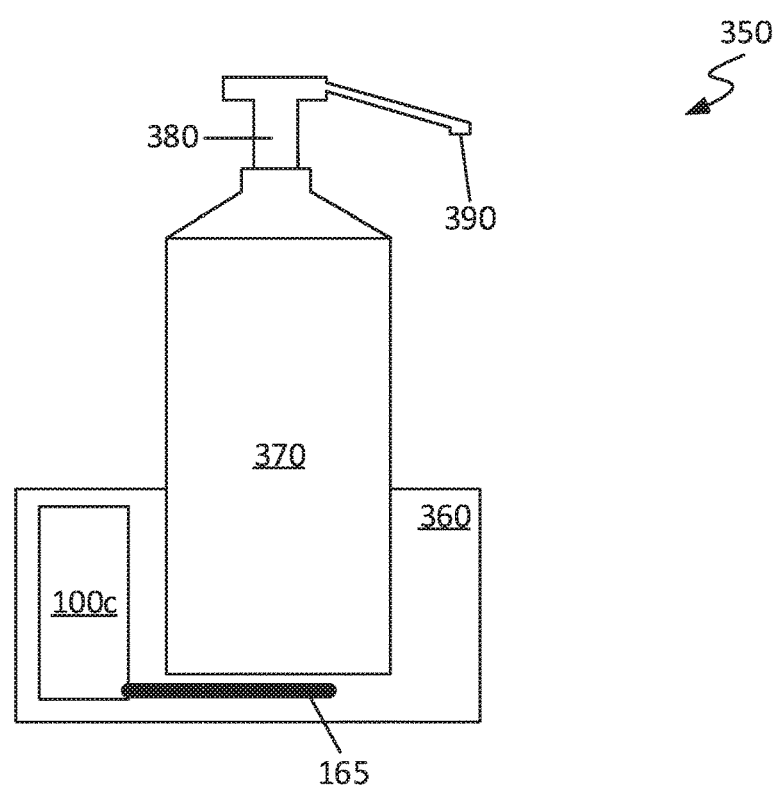
FIG. 4B is a cross-sectional side elevation view of a stand-alone hand sanitizer dispenser unit including an mZone transmitter configured in accordance with an embodiment of the present disclosure.

FIG. 4B is a cross-sectional side elevation view of a stand-alone hand sanitizer dispenser unit 350 including an mZone transmitter 100c configured in accordance with an embodiment of the present disclosure. As can be seen, mZone transmitter 100c may be disposed within base portion 360 such that pressure sensor 165 extends beneath hand sanitizer bottle 370. Activation (e.g., pressing via the hand) of pump portion 380 to dispense hand sanitizer from nozzle portion 390 may impart sufficient pressure on pressure sensor 165 to register dispensation, and that data may be used in recording a hand hygiene compliance event. In response to dispensing the hand sanitizer, mZone transmitter 100c may transmit an mZone signal 142 including data pertaining to the compliance event, which may be received by a beacon tag 10 within transmission range.

As previously noted, wireless transmitter 30 of beacon tag 10 may be configured to output a beacon signal 32, which may be, for example, a Bluetooth signal of a frequency in an ISM band of between 2.4-2.485 GHz. In accordance with some embodiments, beacon signal 32 may be of the Bluetooth 4.0 standard advertising beacon format, which may allow manufacturers to create custom-formatted attribute definitions and data for transmission by wireless transmitter 30. In at least some such cases, a given data packet of beacon signal 32 may be of standard Bluetooth signal length (e.g., thirty-one bytes). As discussed below, beacon signal 32 may include data pertaining to any one, or combination, of a patient mZone, a hand hygiene station mZone, and hand hygiene compliance or non-compliance, in accordance with some embodiments. In some cases, beacon signal 32 may include data pertaining to the presence of the tagged individual and his or her location in a target space. In accordance with some embodiments, this information may be logged to server database 230.

Figure 5:
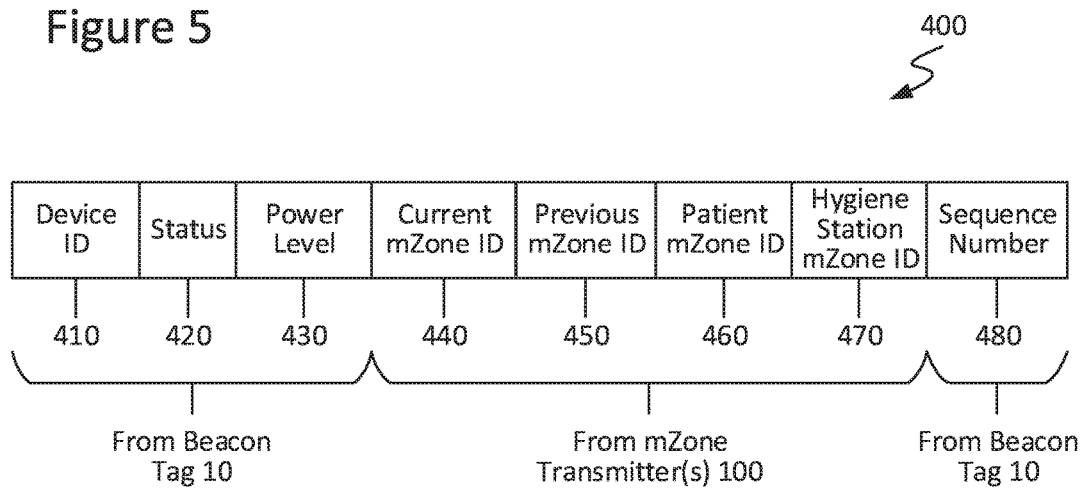
FIG. 5 represents several data fields of a data packet which may be transmitted by beacon tag in a beacon signal, in accordance with an embodiment of the present disclosure

FIG. 5 represents several data fields of a data packet 400 which may be transmitted by beacon tag 10 in a beacon signal 32, in accordance with an embodiment of the present disclosure. As can be seen, in some cases, beacon tag 10 may transmit a data packet 400 including Device ID 410 data. Device ID 410 data may be an identifier (e.g., such as an address or a manufacture code) unique to the source beacon tag 10 transmitting beacon signal 32 and, as such, may be utilized as a unique identifier for each individual hosting a beacon tag 10. In an example case, Device ID 410 data may be 6 bytes in size, though in other cases, lesser or greater byte sizes may be provided, as desired for a given target application or end-use.

In some cases, beacon tag 10 may transmit a data packet 400 including Status 420 data, which may cover any of a wide range of conditions and communications. In some cases, Status 420 data may include data pertaining to hand hygiene compliance or non-compliance events. In some cases, Status 420 data may include data pertaining to the current or most recent status of motion detection sensor 50 (e.g., in a state of motion or having received a detectable impact). In some cases, Status 420 data may include data pertaining to the current or most recent status of wireless receiver 60 (e.g., receiving an mZone signal 142 or in a low-power state). In some cases, Status 420 data may include data pertaining to the current or most recent status of any of the various sensors of beacon tag 10. In an example case, Status 420 data may be 1 byte in size, though in other cases, greater byte sizes may be provided, as desired for a given target application or end-use. Numerous options for data which may be encoded in the Status 420 data of a given data packet 400 of beacon signal 32 will be apparent in light of this disclosure.

In some cases, beacon tag 10 may transmit a data packet 400 including Power Level 430 data. Power Level 430 data may report the current power level of power supply 90 of beacon tag 10 (e.g., as a percentage scale or other quantity). Inclusion of Power Level 430 data in beacon signal 32 may help to provide an early warning if a given beacon tag 10 is running low on power provided by its power supply 90. In accordance with some embodiments, this can be used to guard against power failures of one or more portions of system 1000.

In some cases, beacon tag 10 may transmit a data packet 400 including Current mZone ID 440 data and/or. Previous mZone ID 450 data. In accordance with some embodiments, as beacon tag 10 enters the transmission range of a first mZone transmitter 100 and receives its mZone signal 142, it may pull the mZone ID 520 from that signal 142 and initially store it as Current mZone ID 440 data. As beacon tag 10 leaves the transmission range of the first mZone transmitter 100 and enters the transmission range of a different second mZone transmitter 100, receiving its mZone signal 142, it may pull the mZone ID 520 from that latter mZone signal 142 and store it as Current mZone ID 440 data, transitioning the mZone ID 520 from the first mZone transmitter 100 to being stored as Previous mZone ID 450 data. Thus, the Current mZone ID 440 data and Previous mZone ID 450 data may serve to provide a history for the tracking of the individual hosting beacon tag 10. That is, the Current mZone ID 440 data may include data pertaining to the current location of the beacon tag 10, and the Previous mZone ID 450 data may include data pertaining to the previous location of the beacon tag 10, and thus the individual hosting beacon tag 10 may be tracked at each step of the way. In some example cases, either (or both) of Current mZone ID 440 data and Previous mZone ID 450 data may be 3 bytes in size, though in other cases, lesser or greater byte sizes may be provided, as desired for a given target application or end-use.

In some cases, beacon tag 10 may transmit a data packet 400 including Patient mZone ID 460 data. In accordance with some embodiments, as beacon tag 10 enters the transmission range of an mZone transmitter 100 (e.g., an mZone transmitter 100a) located proximate a patient and receives its mZone signal 142, it may pull the ID of that patient mZone from that signal 142 and store it as Patient mZone ID 460 data. In an example case, Patient mZone ID 460 data may be 3 bytes in size, though in other cases, lesser or greater byte sizes may be provided, as desired for a given target application or end-use.

In some cases, beacon tag 10 may transmit a data packet 400 including Hygiene Station mZone ID 470 data. In accordance with some embodiments, as beacon tag 10 enters the transmission range of an mZone transmitter 100 (e.g., an mZone transmitter 100b, 100c) located proximate a hand hygiene station and receives its mZone signal 142, it may pull the ID of that hand hygiene station mZone from that signal 142 and store it as Hygiene Station mZone ID 470 data. In an example case, Hygiene Station mZone ID 470 data may be 3 bytes in size, though in other cases, lesser or greater byte sizes may be provided, as desired for a given target application or end-use.

In some cases, beacon tag 10 may transmit a data packet 400 including Sequence Number 480 data. In accordance with some embodiments, Sequence Number 480 data may increment each time there is a change to data of beacon signal 32. In an example case, Sequence Number 480 data may be 1 byte in size, though in other cases, greater byte sizes may be provided, as desired for a given target application or end-use.

In some cases, beacon tag 10 may transmit a data packet 400 optionally including additional data. For example, in some instances, data packet 400 optionally may include sensor data, which may originate from any sensor optionally included with beacon tag 10. In a more general sense, and in accordance with some embodiments, data provided by any sensor of beacon tag 10 may be stored in this manner as a portion of a data packet 400 to be transmitted by beacon tag 10 in a beacon signal 32. As previously discussed, some example sources of additional data may include a moisture sensor, a humidity sensor, a proximity sensor, and a magnetic field sensor, among others.

As previously noted, wireless transmitter 140 of mZone transmitter 100 may be configured to output an mZone signal 142. Signal 142 may be of a frequency in any one, or combination, of ISM bands, including 902 MHz, 915 MHz, 894 MHz, 869 MHz, and 433 MHz and, in at least some instances, may be of a proprietary short data packet format. In accordance with some embodiments, a given mZone signal 142 may include a data packet having an mZone type followed by an mZone identifier field. Depending on which type and identifier field are provided, the nature of the mZone signal 142, as well as the operation of a recipient downstream beacon tag 10 (or other downstream element of system 1000), may change accordingly. In some cases, a burst of data packets may be transmitted in mZone signal 142.

As will be appreciated in light of this disclosure, it may be desirable to ensure that a given data packet of a given mZone signal 142 is kept relatively short so that a given beacon tag 10 within range of the source mZone transmitter 100 may receive it (via mZone signal 142) with minimal on-time at a very low duty cycle. In at least some instances, mZone signal 142 may be of a proprietary short data packet format. In accordance with some embodiments, the RF data rate for mZone signal 142 may be sufficiently high to keep mZone signal 142 short enough to be received by the wireless receiver 60 of a given beacon tag 10 within a time window of about 1 ms or less. To this end, several parameters, including modulation scheme and bit rate, may be customized, as desired for a given target application or end-use.

Figure 6:
FIG. 6 represents several data fields of a data packet which may be transmitted by mZone transmitter in an mZone signal, in accordance with an embodiment of the present disclosure.

FIG. 6 represents several data fields of a data packet 500 which may be transmitted by rnZone transmitter 100 in an mZone signal 142, in accordance with an embodiment of the present disclosure. As can be seen, in some cases, mZone transmitter 100 may transmit a data packet 500 including: (1) mZone Type 510 data; and (2) mZone ID 520 data.

The mZone Type 510 data may indicate the type of source mZone transmitter 100 transmitting mZone signal 142 including data packet 500. For instance, mZone Type 510 data may indicate that the source of the mZone signal 142 is either an mZone transmitter 100a (FIG. 3A), an mZone transmitter 100b (FIG. 3B), or an mZone, transmitter 100c (FIG. 3C). More generally, mZone Type 510 data identifies the source mZone transmitter 100 as being programmed to be disposed at and representative of either a patient mZone, a hand hygiene station mZone (e.g., a hand washing station mZone or a hand sanitizer station mZone), an unsanitary mZone, or other mZone location type, in accordance with some embodiments. Thus, mZone Type 510 data may be indicative of location specifically, whether a recipient beacon tag 10 is within transmission range of a hand hygiene station (e.g., hand washing station; hand sanitizer station), a patient zone, an unsanitary zone, or some other zone of interest.

The mZone ID 520 data may be an identifier unique to the source mZone transmitter 100 transmitting mZone signal 142 and, as such, may be utilized as a unique identifier for the location where that mZone transmitter 100 is disposed. Data packet 500 of mZone signal 142 may be received by beacons tag(s) 10 within range, thereby providing those beacon tag(s) 10 with location information in relation to the source mZone transmitter 100 of that mZone signal 142. A beacon tag 10 receiving such an mZone signal 142 may add the mZone ID 520 data (which may be indicative of the source mZone transmitter 100) in the Current mZone ID 440 data field and/or the Previous mZone ID 450 data field of a data packet 400 that it subsequently transmits in its beacon signal 32. In this manner, the location of that beacon tag 10 with respect to one or more mZone transmitters 100 that sourced the received mZone signal(s) 142 may be determined. In an example case, mZone ID 520 data may be 3 bytes in size, though in other cases, lesser or greater byte sizes may be provided, as desired for a given target application or end-use.

Returning to FIG. 1, system 1000 further may include a gateway 200, which may be configured, in accordance with some embodiments, to receive data gathered from beacon tag(s) 10 and/or mZone transmitter(s) 100 and transmit that data to a server database 230 via interne 220. To such ends, gateway 200 may be configured to utilize any one or combination of suitable communication protocols, wired or wireless, such as, for example, Ethernet, Bluetooth, WIFI, and cellular, among others. In accordance with some embodiments, gateway 200 may be any one, or combination, of fixed Bluetooth-to-WIFI, cellular-to-WIFI, or cellular-to-Bluetooth bridge/hub devices. Gateway 200 may be used to read all beacon signal(s) 32 from beacon tag(s) 10, all beacon signal(s) 132 from mZone transmitter(s) 100, and all mZone signals 142 from mZone transmitter(s) 100 within range and to forward the information over a network interface to internet 220 and server database 230. As noted above, in some instances, mZone transmitter 100 may transmit a beacon signal 132 including data pertaining to its operation, such as the current power level of its power supply 190. In accordance with some embodiments, gateway 200 may be configured to receive such a beacon signal 132 and relay information obtained therefrom to server database 230, providing for a mechanism by Which the integrity status of system 1000, in part or in whole, may be determined. Other suitable configurations for gateway 200 will depend on a given application and will be apparent in light of this disclosure.

System 1000 further involve use of a reader device 210, mobile or otherwise, which may be any one, or combination, of a laptop/notebook computer, a sub-notebook computer, a tablet computer, a desktop computer, a mobile phone, a smartphone, a personal digital assistant (PDA), and a cellular handset. In accordance with some embodiments, reader device 210 may be configured for monitoring and controlling operation of any part or the totality of system 1000 and its various constituent elements. In some cases, reader device 210 may be a dedicated reader device configured specifically to such ends, whereas in some other cases, reader device 210 may be a general computing device configured for use to such ends, optionally hosting an application to facilitate its use in monitoring and controlling operation of system 1000. In accordance with some embodiments, reader device 210 may be utilized in assigning/pairing a given beacon tag 10 with a given individual. In accordance with some embodiments, reader device 210 may pull from server database 230 any user-designated names of beacon tags 10 and mZone transmitters 100 and display them for user review, thereby facilitating the user's understanding of which specific tagged individuals and which specific locations through which the tagged individuals have traveled are being considered. In some embodiments, reader device 210 may be configured to read beacon tags 10, which keep a status count of both compliant and non-compliant hand hygiene-related events.

In accordance with some embodiments, reader device 210 may be configured to transmit a control signal 132 to a given mZone transmitter 100 and, at least in some embodiments, may host an application or other software specifically to that end. In at least some cases, such a control signal 132 may be of the Bluetooth 4.0 standard protocol specification to connect and transfer data between reader device 210 and mZone transmitter 100. In accordance with some embodiments, control signal 132 may instruct a recipient mZone transmitter 100 to transmit an mZone signal 142 including data packet 500. In accordance with some embodiments, reader device 210 may be configured to communicate with a given mZone transmitter 100 via control signal 132 in programming it to serve as an mZone transmitter 100a at a patient mZone or an unsanitary mZone, an mZone transmitter 100b at a hand washing station mZone, or an mZone transmitter 100c at a hand sanitizer dispenser station mZone. Other suitable configurations for a given reader device 210 will depend on a given application and will be apparent in light of this disclosure.

Server database 230, which may be accessible through the internet 220, may be cloud-based, in part or in whole. As a means of data storage, server database 230 may be configured to store information saved thereat, for instance, by any of mZone transmitter(s) 100, beacon tag(s) 10, reader device(s) 210, and computing device(s) 240. In accordance with some embodiments, server database 230 may store compliance data and timestamps of all reported compliant and non-compliant hand hygiene events. In some instances, server database 230 may be configured to issue alerts and other notifications pertaining to hand hygiene-related events, in some cases based on user-configurable criteria. In an example case, server database 230 may store information about assignment/pairing of a given beacon tag 10 with a given individual, which may be retrieved by reader device 210 or computing device 240, for example. In another example case, server database 230 may store information about user-designated familiar names for beacon tags 10 and mZone transmitters 100, which may be retrieved by reader device 210 or computing device 240, for example. That is, reader device 210 may read the actual Device II) 410 (from a beacon tag 10) or mZone ID 520 (from an mZone transmitter 100), compare that with data on server database 230, and pull the designated familiar name from server database 230 for review by the user, helping to ensure that the user understands which elements of system 1000 are being considered at a time. In accordance with some embodiments, server database 230 may be configured to verify that system 1000 is properly working and that the battery or other power supply status of all beacon tags 10 and mZone transmitters 100 is good. Thus, server database 230 may be used to monitor mZone transmitter(s) 100 to determine whether there is need to replace any given power supply 190. In a more general sense, server database 230 may allow for a given desired degree of inter-networking of the components of system 1000 and other elements as part of the internet of things (IOT), in accordance with some embodiments. Also, as will be appreciated in light of this disclosure, timekeeping data obtained via system 1000 and stored via server database 230 additionally, or alternatively, may be used, for example, in monitoring personnel timekeeping requirements and payroll, in accordance with some embodiments. Other suitable configurations for server database 230 will depend on a given application and will be apparent in light of this disclosure.

Computing device 240 may be any one, or combination, of a Laptop/notebook computer, a sub-notebook computer, a tablet computer, a desktop computer, a mobile phone, a smartphone, a PDA, a cellular handset, a television set, a computer monitor, and a video conferencing system. Computing device 240 may be configured for communication with server database 230 utilizing wired communication via Universal Serial Bus (USB), Ethernet, FireWire, or other wired communicating interfacing, wireless communication via. WIFI, Bluetooth, or other wireless communication interfacing, or a combination of any thereof. In accordance with some embodiments, computing device 240 may host a browser or other software application configured to facilitate review of information pertinent to any part or the totality of system 1000 and its various constituent elements. In accordance with some embodiments, computing device 240 may be used to retrieve and display hand hygiene compliance statistical data periodically or otherwise as desired. Computing device 240 may be configured, in accordance with some embodiments, to access server database 230 to display the current and/or previous location of a given individual tagged with a beacon tag 10, based on the fixed location of reported mZone transmitters 100. In some cases, computing device 240 and reader device 210 may be the same device. Other suitable configurations for computing device 240 will depend on a given application and will be apparent in light of this disclosure.

In accordance with some embodiments, a given mZone transmitter 100 may send a data packet 500 in an mZone signal 142 over any one, or combination, of ISM bands, including 915 MHz, 902 MHz, 894 MHz, 869 MHz, and 433 MHz. The data packet 500 may include, among other data, an identification code (e.g., mZone ID 520) of the relevant source mZone transmitter 100. Beacon tag(s) 10 within transmission range may receive that mZone signal 142 and pull data from the received mZone signal 142. Because the source mZone transmitter 100 is in a fixed position, the location of the beacon tag 10 can be mapped to be within transmission range of that mZone transmitter 100. Thus, mZone ID 520, received by beacon tag 10, may serve as an indicator that the beacon tag 10, and thus the tagged individual, is proximate the specific mZone transmitter 520 having that mZone ID 520. A given recipient beacon tag 10 then may relay that identifier data, along with data of its own, via a transmitted beacon signal 32, which may be received by gateway 200 and/or a reader device 210. When gateway 200 receives the beacon signal 32, it may deliver data from beacon signal 32 to server database 230 (via the internet 220), where it may be viewed, for instance, by a computing device 240 via a web browser or other suitable means and/or by a reader device 210 having access to server database 230.

In accordance with some embodiments, a given mZone transmitter 100 may be disposed at a given fixed or otherwise designated location. In some embodiments, a given mZone transmitter 100 may be configured to operate only as a single type of mZone transmitter device. In this manner, such an mZone transmitter 100a, 100b, or 100c of a dedicated type may be chosen and deployed at a given target location based on the applicable monitoring context.

In some other embodiments, however, an mZone transmitter 100 may be configured to operate as any of a plurality of types of mZone transmitters any one, or combination, of mZone transmitters 100a, 100b, and 100c. In this manner, an mZone transmitter 100 of an undedicated type may be deployed at a given target location and programmed based on the applicable monitoring context, assuming the inclusion of any componentry required for a given desired mZone transmission capability (e.g., proximity sensor 152; pressure sensor 165). For instance, if such an mZone transmitter 100 includes or has access to a proximity sensor 152, then it optionally can be programmed to operate as an mZone transmitter 100b, as described herein, in accordance with some embodiments. If the mZone transmitter 100 includes or has access to a pressure sensor 165, then it optionally can be programmed to operate as an mZone transmitter 100c, as described herein, in accordance with some embodiments. In some still other instances, mZone transmitter 100 optionally can be programmed to operate as an mZone transmitter 100a, as described herein, in accordance with some embodiments. Selection or other designation of a given operation modality, standard or customized, for such a multi-mode mZone transmitter 100 may be made, in accordance with some embodiments, via a control signal 132 received from a reader device 210. In this manner, a singular mZone transmitter 100 may be deployable to various mZone monitoring ends in various target locations, as desired for a given target application or end-use.

In accordance with some embodiments, a dedicated mZone transmitter 100a (or mZone transmitter 100 programmed to function as an mZone transmitter 100a) may be deployed at a designated patient mZone, such as at a patient's bed or chair. In accordance with some embodiments, a dedicated mZone transmitter 100a (or mZone transmitter 100 programmed to function as an mZone transmitter 100a) may be deployed at a doorway to a patient's room or a bathroom. In accordance with some embodiments, a dedicated mZone transmitter 100a (or mZone transmitter 100 programmed to function as an mZone transmitter 100a) may be deployed at a designated unsanitary zone, such as trash cans, laundry carts, medical waste disposal receptacles, pieces of medical equipment, and computer terminals, to name a few examples.

In accordance with some embodiments, a dedicated mZone transmitter 100b (or mZone transmitter 100 programmed to function as an mZone transmitter 100b) may be deployed at a sink or other hand washing station. Proximity sensor 152 may serve, in accordance with some embodiments, to detect the presence of the individual tagged with beacon tag 10 at the hand washing station.

In accordance with some embodiments, a dedicated mZone transmitter 100c (or mZone transmitter 100 programmed to function as an mZone transmitter 100c) may be deployed at a hand sanitizer station, whether of dispenser unit form or pump bottle form. Pressure sensor 165 may serve, in accordance with some embodiments, to detect operation of the hand sanitizer dispenser 300 by the individual tagged with beacon tag 10.

To pair a beacon tag 10 with a given individual, the beacon tag 10 of interest may be identified in any of several ways. For instance, in accordance with some embodiments, the beacon tag 10 may receive an impact (e.g., such as a double-tap on housing 20), in response it may output a beacon signal 32 that includes data making it easier for a reader device 210 to identify that beacon tag 10 to be paired with the individual to host it. In accordance with some other embodiments, the beacon tag 10 may be held proximate reader device 210 and, because the signal strength of beacon signal 32 would be above a designated threshold level, it would be easy for reader device 210 to identify that beacon tag 10 to be paired with the individual to host it. In some cases, the individual's name may be entered or selected on reader device 210. In some other cases, reader device 210 may be used to scan a code (e.g., bar code, QR code, NFC tag, and so on) associated with the individual. Optionally, a user may input a familiar name and other custom information pertinent to the beacon tag 10 and individual being paired to help facilitate review and management of the various elements of system 1000. Thereafter, the pairing and naming information may be sent to server database 230, where it may be stored for subsequent retrieval in operation of system 1000.

To mark the current location of a tagged individual, with a reader device 210 near the individual tagged with a beacon tag 10, motion detection sensor 50 or other on-board sensor may be used to generate a signal to notify beacon tag 10 to mark the current location, in accordance with some embodiments. This may cause beacon tag 10 to send out a beacon signal 32 with data pertaining to the desired marked location in Status 420 field, which is received by reader device 210, and using a GPS in reader device 210, the location of the tagged individual may be recorded and sent to server database 230, in accordance with some embodiments.

Example Applications

As will be appreciated in light of this disclosure, system 1000 may be utilized in tracking hand hygiene compliance in a given target space, such as a hospital, laboratory, or restaurant, among others. To such ends, beacon tag 10 may be programmed with state machine logic providing for one or more compliance modes applicable to a given hand hygiene compliance context. A given compliance mode may consist of various rules and timers, which may be standard, custom, or proprietary, as desired for a given target application or end-use. Programming of such compliance mode(s) may be native to beacon tag 10 (e.g., in processor 40 and/or memory 45) or performed by an external controller, such as a reader device 210, sending a signal to beacon tag 10. In accordance with some embodiments, selection of a given compliance mode may occur in real time based on the current activities and location of an individual tagged with beacon tag 10. As previously discussed, beacon tag 10 may be configured, in accordance with some embodiments, to read the different mZone Type 510 data and mZone 11) 520 received in an mZone signal 142 transmitted by a given source mZone transmitter 100. Thus, for purposes of hand hygiene compliance monitoring in a given context and target space, selection of a given compliance protocol may be made by beacon tag 10 based on its receiving of one or more mZone signals 142 including data pertaining to the source mZone transmitter(s) 100 nearby.

Figure 7:
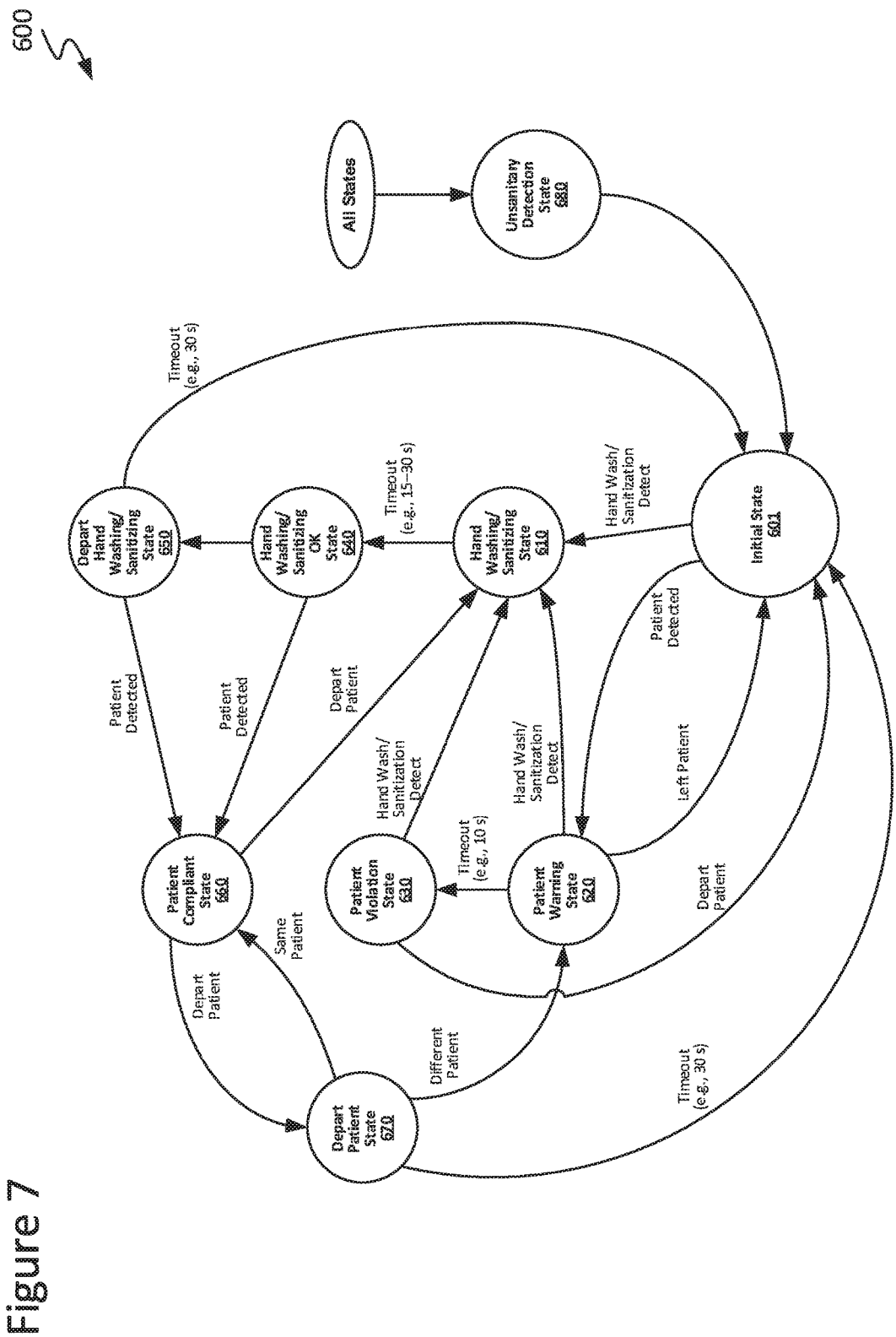
FIG. 7 is a state diagram representing state machine logic for hand hygiene compliance in a patient-based context, in accordance with an embodiment of the present disclosure.
Figure 8:
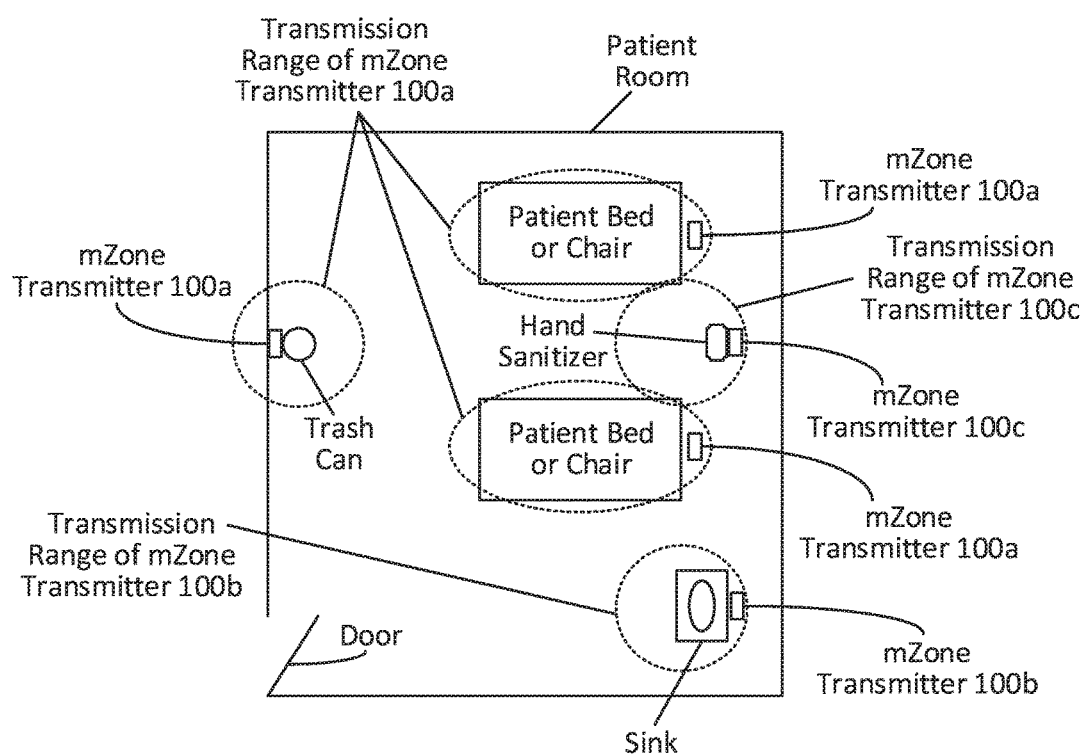
FIG. 8 is a top-down plan view of a patient room illustrating an example implementation of a wireless hand hygiene tracking system, in accordance with an embodiment of the present disclosure.

FIG. 7 is a state diagram representing state machine logic 600 for hand hygiene compliance in a patient-based context, in accordance with an embodiment of the present disclosure. To facilitate explanation of state machine logic 600, further consider FIG. 8, which is a top-down plan view of a patient room illustrating an example implementation of system 1000, in accordance with an embodiment of the present disclosure. In the example case illustrated via FIG. 8, there is an mZone transmitter 100a disposed at each of the patient beds or chairs, as well as a trash can within the patient's room. Also, within the patient's room, an mZone transmitter 100b is disposed at a sink, and an mZone transmitter 100c is disposed at a hand sanitizer dispenser 300, 350.

As can be seen in FIG. 7, initial State 601 may be the default state of state machine logic 600. In accordance with some embodiments, Initial State 601 may be representative of a default unsanitary condition of an individual tagged with beacon tag 10. When the tagged individual first enters the patient's room, state machine logic 600 may be in Initial State 601 by default. If the tagged individual proceeds to a hand hygiene station within the patient's room, he may enter the transmission range of an mZone transmitter 100 deployed thereat. As previously discussed, if the hand hygiene station is a hand washing station, an mZone transmitter 100b may be deployed thereat. If instead the hand hygiene station is hand sanitizing station, an mZone transmitter 100c may be deployed thereat. In either case, upon entering the transmission range of mZone transmitter 100b, 100c, beacon tag 10 may receive an mZone signal 142 transmitted thereby and may transition state machine logic 600 from Initial State 601 to Hand Washing/Sanitizing State 610.

In Hand Washing/Sanitizing State 610, if the hand hygiene station is, for example, a sink or other hand washing station having an mZone transmitter 100b disposed thereat, then proximity sensor 152 may detect the physical presence of the tagged individual. Timer 155 of mZone transmitter 100b may track the amount of time that the tagged individual remains at the hand washing station. After a threshold time limit (e.g., about 15-30 s) passes, as measured by timer 155 in concert with proximity sensor 152, wireless transmitter 140 of mZone transmitter 100b may transition out of a low-power state (e.g., a sleep-state or an off-state) and transmit, in an mZone signal 142, a data packet 500 including mZone Type 510 data and mZone ID 520 data pertaining to that mZone transmitter 100b. If beacon tag 10 is within transmission range, then it may receive that mZone signal 142 and transition to Hand Washing/Sanitizing OK State 640 (discussed below). Also, in some cases, the tagged individual may be provided with one or more types of feedback indicative of his current hand hygiene compliance status. For instance, mZone transmitter 100b may emit light of a first color (e.g., red) via a first optical output device 185 when proximity sensor 152 detects sufficient proximity of the tagged individual. Additionally, mZone transmitter 100b may emit light of a second color (e.g., green) via a second optical output device 185 when the designated threshold time limit for the duration of the presence of the tagged individual has been met or exceeded. Alternatively, or additionally, mZone transmitter 100b may emit one or more sounds via an audio output device 180 to such ends.

If instead the hand hygiene station is, for example, a hand sanitizer dispenser 300, 350 having an mZone transmitter 100c disposed thereat, then pressure sensor 165 may detect activation of the dispenser 300, 350 by the tagged individual. Because the designated threshold time limit may not be applicable in the relatively brief context of dispensing a hand sanitizer, timer 155 of mZone transmitter 100c may remain at zero, be kept in a low-power state (e.g., an off-state or sleep-state), or may be omitted from mZone transmitter 100c altogether. Upon pressure sensor 165 detecting sufficient applied pressure causing hand sanitizer dispenser unit 300, 350 to dispense hand sanitizer, wireless transmitter 140 of mZone transmitter 100c may transition out of a low-power state (e.g., a sleep-state or an off-state) and transmit, in an mZone signal 142, a data packet 500 including mZone Type 510 data and mZone ID 520 data pertaining to that mZone transmitter 100c. If beacon tag 10 is within transmission range, then it may receive that mZone signal 142 and transition to Hand Washing/Sanitizing OK State 640 (discussed below).

When the tagged individual approaches a patient (e.g., at a patient bed or chair), he may enter the transmission range of an mZone transmitter 100a deployed thereat. If the tagged individual enters the transmission range of that mZone transmitter 100a without first going to a hand hygiene station, where he would have entered the transmission range of an mZone transmitter 100b, 100c and received an mZone signal 142 including a data packet 500 having data pertinent thereto, then beacon tag 10 may transition state machine logic 600 from initial State 601 to Patient Warning State 620 rather than to Hand Washing/Sanitizing State 610.

In Patient Warning State 620, if the tagged individual departs from the transmission range of that mZone transmitter 100a (e.g., the patient mZone) within a designated time window (e.g., about 10 s or less) and does not return, then beacon tag 10 may transition state machine logic 600 from Patient Warning State 620 back to Initial State 601. If instead the tagged individual departs from the patient mZone within the designated time window and proceeds to a hand hygiene station where he may enter the transmission range of an mZone transmitter 100b, 100c deployed thereat, then beacon tag 10 may receive an mZone signal 142 including a data packet 500 having data pertinent thereto and transition state machine logic 600 from Patient Warning State 620 to Hand Washing/Sanitizing State 610, as previously discussed.

If, however, the tagged individual remains within the patient mZone beyond the designated time window, then beacon tag 10 may transition state machine logic 600 from Patient Warning State 620 to Patient Violation State 630. In Patient Violation State 630, beacon tag 10 may provide feedback to the tagged individual in effort to remedy the hand hygiene non-compliance. For instance, beacon tag 10 may emit sound (e.g., via an audio output device 80), light (e.g., via an optical output device 85), and/or vibration (e.g., via a vibratory output device) indicative of the non-compliance event. Upon the occurrence of a non-compliance event, beacon tag 10 may transmit, in a beacon signal 32, a data packet 400 including Status 420 data pertaining to the hand hygiene violation event. A gateway 200 receiving that beacon signal 32 may forward information pertaining to the non-compliant event to server database 230 (e.g., via the internet 220). In this manner, a non-compliant event may be registered by beacon tag 10 and logged by server database 230.

If, after a hand hygiene violation, the tagged individual does not depart the patient mZone, then he may remain in the Patient Violation State 630. If, however, the tagged individual departs from the patient mZone and does not return, then beacon tag 10 may transition state machine logic 600 from Patient Warning State 620 back to Initial State 601. Still further, if the tagged individual instead proceeds to a hand hygiene station, entering the transmission range of mZone transmitter 100b, 100c, then beacon tag 10 may receive an mZone signal 142 transmitted thereby and may transition state machine logic 600 from Patient Violation State 630 to Hand Washing/Sanitizing State 610 and then Hand Washing/Sanitizing OK State 640, as previously discussed.

If a tagged individual in Hand Washing/Sanitizing OK State 640 proceeds promptly to a patient mZone, he may enter the transmission range of am mZone transmitter 100a disposed thereat, and beacon tag 10 may receive an mZone signal 142 transmitted thereby and transition state machine logic 600 from Hand Washing/Sanitizing OK State 640 to Patient Compliant State 660. In Patient Compliant State 660, beacon tag 10 may provide feedback alerting the tagged individual that hand hygiene compliance has been achieved. For instance, beacon tag 10 may emit sound (e.g., via an audio output device 80), light (e.g., via an optical output device 85), and/or vibration (e.g., via a vibratory output device) indicative of the compliance event. Upon the occurrence of a compliance event, beacon tag 10 may transmit, in a beacon signal 32, a data packet 400 including Status 420 data pertaining to the hand hygiene compliance. A gateway 200 receiving that beacon signal 32 may forward information pertaining to the compliant event to server database 230 (e.g., via the interne 220). In this manner, a compliant event may be registered by beacon tag 10 and logged by server database 230.

If, however, a tagged individual in Hand Washing/Sanitizing OK State 640 does not proceed promptly to a patient mZone, then beacon tag 10 temporarily may transition state machine logic 600 from Hand Washing OK State 640 to Depart Hand Washing/Sanitizing State 650. Once in Depart Hand Washing/Sanitizing State 650, if the tagged individual proceeds to a patient rnZone within a designated time window (e.g., about 15-30 s), then beacon tag 10 may transition state machine logic 600 from Hand Washing/Sanitizing State 650 to Patient Compliant State 660, as discussed above. If, however, the tagged individual does not proceed to a patient mZone within the designated time window, then beacon tag 10 may reset state machine logic 600 from Depart Hand Washing/Sanitizing State 650 to Initial State 601.

In the Patient Compliant State 660, if the tagged individual departs from the patient mZone, then beacon tag 10 may transition state machine logic 600 from Patient Compliant State 660 to Depart Patient State 670. In the Depart Patient State 670, if the tagged individual returns to the same patient mZone within a designated threshold time limit (e.g., about 30-45 s), as measured by timer 55 of beacon tag 10, then beacon tag 10 may transition state machine logic 600 from Depart Patient State 670 back to Patient Compliant State 660. If instead the tagged individual departs from the patient mZone and does not return to that same patient mZone within the designated threshold time limit, then beacon tag 10 may reset state machine logic 600 from Depart Patient State 670 to initial State 601. If, however, the tagged individual departs from the patient mZone and enters a different patient mZone, then beacon tag 10 may transition state machine logic 600 from Depart Patient State 670 to Patient Warning State 620, where the state machine logic 600 may proceed as discussed above.

From any current state of state machine logic 600, if beacon tag 10 receives an mZone signal 142 from any mZone transmitter 100a deployed, for example, at an unsanitary mZone, then beacon tag 10 may transition to Unsanitary Detect State 680 and then reset to Initial State 601 (e.g., the default unsanitary condition).

Figure 9A:
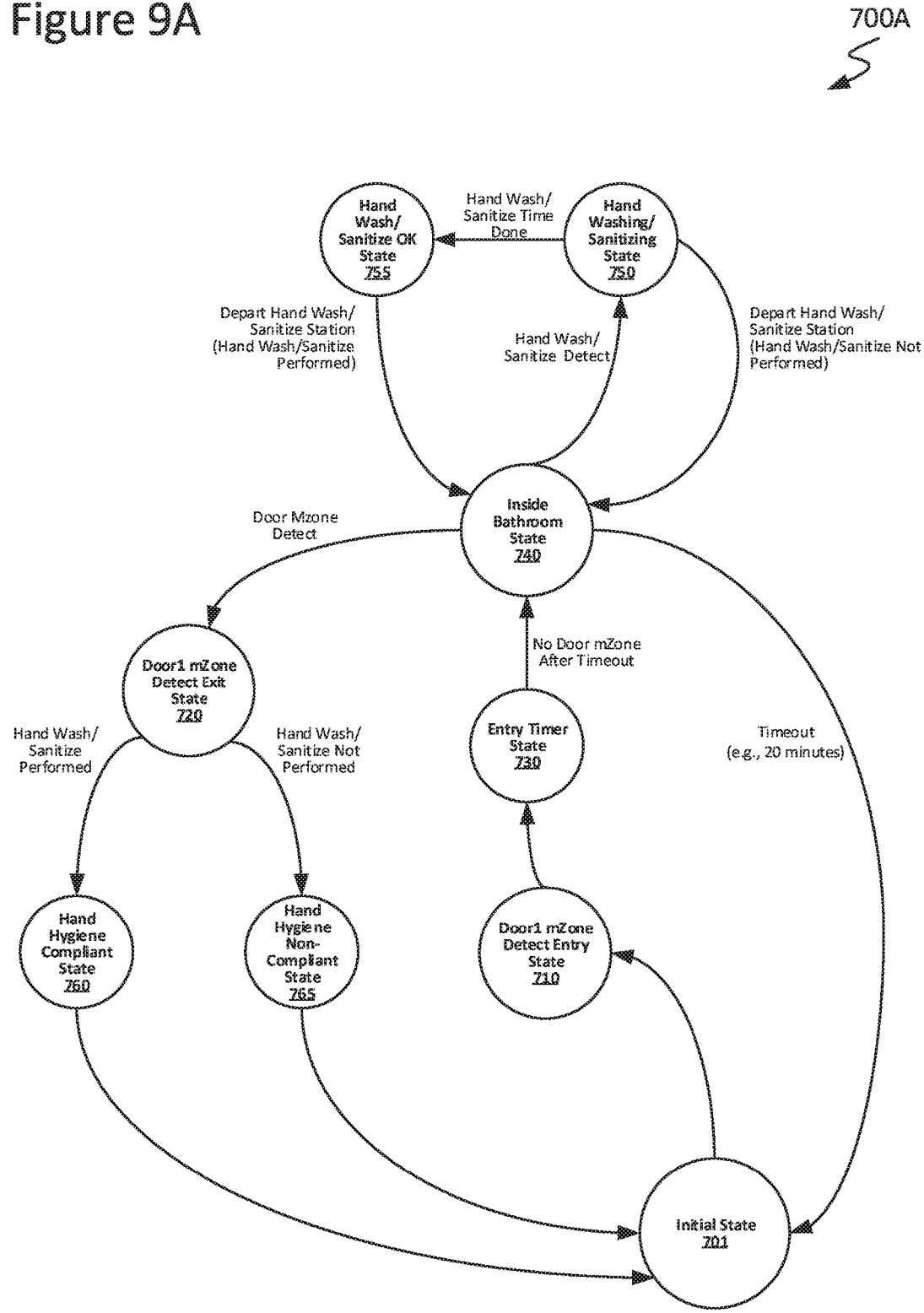
FIG. 9A is a state diagram representing state machine logic for hand hygiene compliance in a bathroom-based context, in accordance with an embodiment of the present disclosure.
Figure 9B:
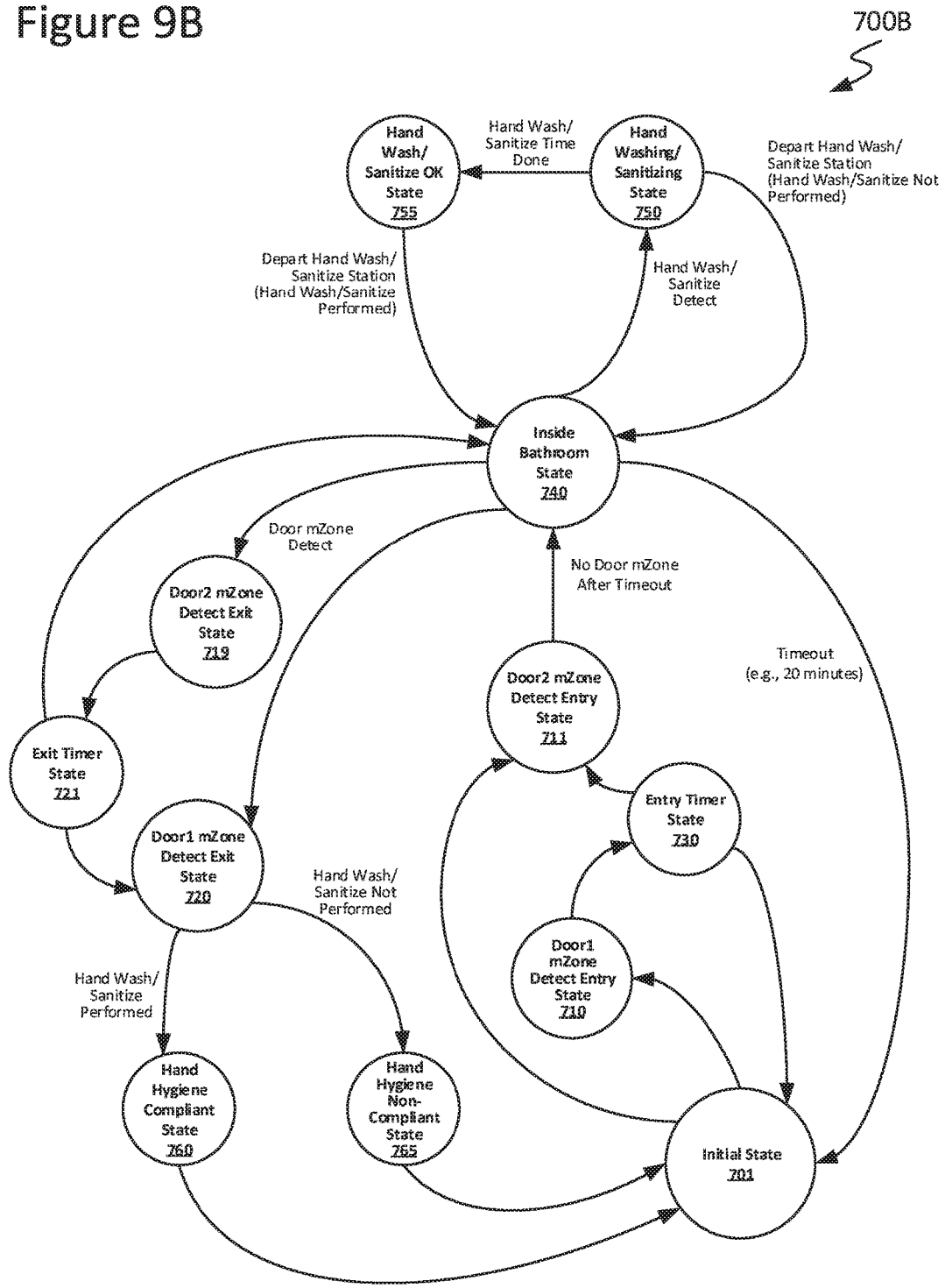
FIG. 9B is a state diagram representing state machine logic for hand hygiene compliance in a bathroom-based context, in accordance with another embodiment of the present disclosure.
Figure 10:
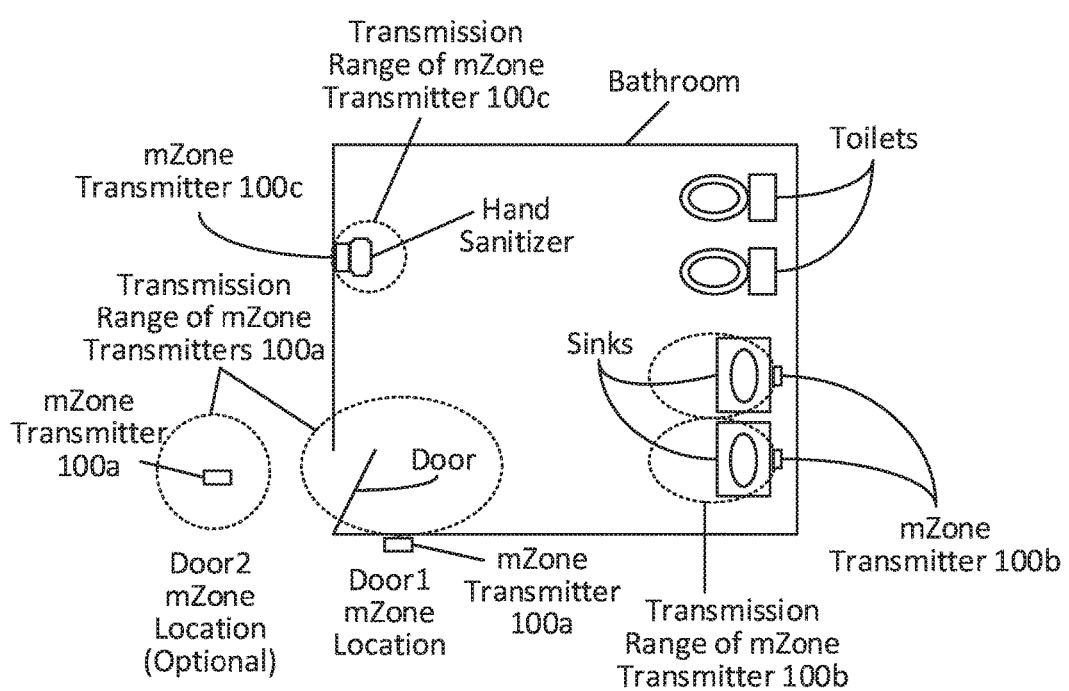
FIG. 10 is a top-down plan view of a bathroom illustrating an example implementation of a wireless hand hygiene tracking system, in accordance with an embodiment of the present disclosure.

FIG. 9A is a state diagram representing state machine logic 700a for hand hygiene compliance in a bathroom-based context, in accordance with an embodiment of the present disclosure. FIG. 9B is a state diagram representing state machine logic 700b for hand hygiene compliance in a bathroom-based context, in accordance with another embodiment of the present disclosure. For consistency and ease of understanding of the present disclosure, state machine logic 700a and 700b may be collectively referred to generally as state machine logic 700, except where separately referenced. To facilitate explanation of state machine logic 700, further consider FIG. 10, which is a top-down plan view of a bathroom illustrating an example implementation of system 1000, in accordance with an embodiment of the present disclosure. In the example case illustrated via FIG. 10, there are two separate mZone transmitters 100a disposed at the doorway of the bathroom. For most monitoring scenarios, inclusion of a single mZone transmitter 100a at an entry/exit point of the bathroom may suffice. However, if two (or more) mZone transmitters 100a are placed in sequential (e.g., tandem) positions relative to an entry/exit point, additional ingress and egress information may be acquired, depending on the order in which the mZone transmitters 100a are read by beacon tag 10. Also, within the bathroom, an mZone transmitter 100b is disposed at each sink, and an mZone transmitter 100c is disposed at a hand sanitizer station.

As can be seen in FIGS. 9A-9B, Initial State 701 may be the default state of state machine logic 700. In accordance with some embodiments, Initial State 701 may be representative of an individual tagged with beacon tag 10 being located outside of a bathroom. When the tagged individual enters the bathroom, he may enter the transmission range of one or more mZone transmitters 100a disposed thereat, and beacon tag 10 may receive mZone signal(s) 142 transmitted thereby and transition state machine logic 700 from Initial State 701 to either Door1 mZone Detect Entry State 710 (e.g., as in the case of state machine logic 700a) or, if a plurality of mZone transmitters 100a is present, Door2 mZone Detect Entry State 711 (e.g., as in the case of state machine logic 700b). Depending on the size of the bathroom, a second mZone transmitter 100a may be placed, for example, outside the door to trigger an in-door or out-door transition, though this is not required.

Once inside the bathroom, beacon tag 10 may transition state machine logic 700 from Door1 mZone Detect Entry State 710 to Entry Timer State 730. In Entry Timer State 730, after a threshold time limit (e.g., about 5-10 s) passes, as measured by timer 55 of beacon tag 10, the tagged individual may be determined to be located inside the bathroom. Consequently, beacon tag 10 may transition state machine logic 700 from Entry Timer State 730 to Inside Bathroom State 740.

From Inside Bathroom State 740, the tagged individual may be required to wash or sanitize his hands before leaving the bathroom, or else a hand hygiene violation will be recorded against him. Although the tagged individual may remain within the bathroom for an undetermined amount of time, upon proceeding to one of the sinks, the tagged individual may enter the transmission range of an mZone transmitter 100b deployed thereat. There, beacon tag 10 may receive an mZone signal 142 from the mZone transmitter 100b and transition state machine logic 700 from Inside Bathroom State 740 to Hand Washing/Sanitizing State 750.

At the sink, proximity sensor 152 may detect the physical presence of the tagged individual, and timer 155 of mZone transmitter 100b may track the amount of time that the tagged individual remains at the sink. After a threshold time limit (e.g., about 15-30 s) passes, as measured by timer 155 in concert with proximity sensor 152, wireless transmitter 140 of mZone transmitter 100b may transition out of a low-power state (e.g., a sleep-state or an off-state) and transmit, in an mZone signal 142, a data packet 500 including mZone Type 510 data and mZone ID 520 data pertaining to that mZone transmitter 100b. Beacon tag 10 may receive that mZone signal 142 and transition state machine logic 700 from Hand Washing/Sanitizing State 750 to Hand Washing/Sanitizing OK State 755.

If instead the hand hygiene station is, for example, a hand sanitizer dispenser 300, 350 having an mZone transmitter 100c disposed thereat, then pressure sensor 165 may detect activation of the dispenser 300, 350 by the tagged individual. Because the designated threshold time limit may not be applicable in the relatively brief context of dispensing a hand sanitizer, timer 155 of mZone transmitter 100c may remain at zero, be kept in a low-power state (e.g., an off-state or sleep-state), or may be omitted altogether from mZone transmitter 100c. Upon pressure sensor 165 detecting sufficient applied pressure causing hand sanitizer dispenser unit 300, 350 to dispense hand sanitizer, wireless transmitter 140 of mZone transmitter 100b may transition out of a low-power state (e.g., a sleep-state or an off-state) and transmit, in an mZone signal 142, a data packet 500 including mZone Type 510 data and mZone ID 520 data pertaining to that mZone transmitter 100c. If beacon tag 10 is within transmission range, then it may receive the rnZone signal 142 transmitted by mZone transmitter 100c and transition state machine logic 700 from Hand Washing/Sanitizing State 750 to Hand Washing/Sanitizing OK State 755. If, however, the tagged individual does not remain at the sink for sufficient time or does not activate a hand sanitizer dispenser, beacon tag 10 may transition state machine logic 700 from Hand Washing/Sanitizing State 750 back to Inside Bathroom State 740, as discussed above, without achieving Hand Washing/Sanitizing OK State 755.

Upon once again receiving an mZone signal 142 from an mZone transmitter 100*a* deployed at the Door2 mZone, beacon tag 10 may transition state machine logic 700 from Inside Bathroom State 740 to Door2 mZone Detect Exit State 719. From there, beacon tag 10 may transition state machine logic 700 from Door2 mZone Detect Exit State 719 to Exit Timer. State 721. In Exit Timer State 721, after a threshold time limit (e.g., about 5-10 s) passes, as measured by timer 55 of beacon tag 10, the tagged individual may be determined to be located outside the bathroom. Alternatively, or additionally, upon once again receiving an mZone signal 142 from an mZone transmitter 100*a* deployed at the Door1 mZone, beacon tag 10 may transition state machine logic 700 from Inside Bathroom State 740 to Door1 mZone Detect Exit State 720.

In detecting the Door1 mZone by receiving an mZone signal 142 from an mZone transmitter 100*a* deployed thereat, beacon tag 10 may transition state machine logic 700 from Door1 mZone Detect Exit State 720 to either Hand Hygiene Compliant State 760 or Hand Hygiene Non-Compliant State 765. If the state machine logic 700 enters the Hand Hygiene Non-Compliant State 765 because Hand Washing/Sanitizing OK State 755 was not previously achieved, beacon tag 10 may provide feedback to the tagged individual in effort to remedy the hand hygiene non-compliance. For instance, beacon tag 10 may emit sound (e.g., via an audio output device 80), light (e.g., via an optical output device 85), and/or vibration (e.g., via a vibratory output device) indicative of the non-compliance event. Upon the occurrence of a non-compliance event, beacon tag 10 may transmit, in a beacon signal 32, a data packet 400 including Status 420 data pertaining to the hand hygiene violation event. A gateway 200 receiving that beacon signal 32 may forward information pertaining to the non-compliant event to server database 230 (e.g., via the internet 220). In this manner, a non-compliant event may be registered by beacon tag 10 and logged by server database 230.

As will be appreciated in light of this disclosure, state machine logic 600, 700 may be modified by changing the various timers or augmented with additional or fewer states, depending on the compliance rules desired for a given target space, in accordance with some other embodiments. The various timeout periods of the state machine logic described herein may be programmed, for instance, depending on the usage rules at the patient mZone or bathroom mZone site or as otherwise desired for a given target application or end-use.

As will be further appreciated in light of this disclosure, because beacon tag 10 is hosted by a tagged individual, system 1000 may be used in locating and tracking the tagged individual in a given target space. In this manner, system 1000 may be utilized, for example, in determining personnel presence and location within a facility. Moreover, system 1000 may be utilized, for example, to record how long tagged employees spend with a given patient, are on a break, or are not in their required designated areas. This information may be useful, for example, as input to a payroll timing system. In accordance with some embodiments, because beacon tag 10 is hosted by a tagged individual, if that individual is a patient, for instance, in a dialysis clinic, then the patient's weight before and after dialysis can be logged automatically by detecting the ID on the scale. Numerous example use cases and system configurations will be apparent in light of this disclosure.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more limitations as variously disclosed or otherwise demonstrated herein.

What is claimed is:

1. A wireless hand hygiene compliance tracking system comprising:
   a micro-zone transmitter device configured to transmit a first signal including data pertaining to a unique identifier associated with the micro-zone transmitter device and a type of the micro-zone transmitter device, wherein:
      the type of the micro-zone transmitter device is indicative of whether the micro-zone transmitter device is configured to be deployed at a patient zone, an unsanitary zone, a hand washing station zone, or a hand sanitizing station zone; and
      the first signal is of a frequency in at least one of a 902 MHz ISM band, a 915 MHz ISM band, an 869 MHz ISM band, an 894 MHz ISM band, and a 433 MHz ISM band; and
   a beacon tag device comprising:
      a wireless receiver configured to receive the first signal transmitted by the micro-zone transmitter device that includes the data pertaining to the unique identifier associated with the micro-zone transmitter device and the type of the micro-zone transmitter device;
      a wireless transmitter configured to transmit a second signal of a frequency in an ISM band of between 2.4-2.485 GHz, wherein the second signal includes data pertaining to:
         a unique identifier associated with the beacon tag device;
         the unique identifier associated with the micro-zone transmitter device;
         the type of the micro-zone transmitter device; and
         either a hand hygiene compliance status or a hand hygiene non-compliance status; and
      a motion detection sensor configured to detect at least one of movement of the beacon tag device and an impact to the beacon tag device and, in response thereto, output a wake-up signal causing the wireless transmitter to transmit the second signal external to the beacon tag device.

2. The wireless tracking system of claim 1, wherein the second signal further includes data pertaining to at least one of:
   a unique identifier associated with the patient zone at which the micro-zone transmitter device is configured to be deployed;
   a unique identifier associated with the hand washing station zone at which the micro-zone transmitter device is configured to be deployed; and
   a unique identifier associated with the hand sanitizing station zone at which the micro-zone transmitter device is configured to be deployed.

3. The wireless tracking system of claim 2, wherein the second signal further includes data pertaining to at least one of:

a status of the beacon tag device;
a power level of a power supply of the beacon tag device; and
an output of a sensor of the beacon tag device.

4. The wireless tracking system of claim 1, wherein the micro-zone transmitter device:
is configured to be deployed at the hand washing station zone; and
further comprises:
a proximity sensor configured to detect a physical presence of an individual tagged with the beacon tag device at the hand washing station zone; and
a timer configured to track a time elapsed during detection of the physical presence of the individual tagged with the beacon tag device at the hand washing station zone.

5. The wireless tracking system of claim 1, wherein the micro-zone transmitter device:
is configured to be deployed at the hand sanitizing station zone; and
further comprises a pressure sensor configured to detect activation of a hand sanitizer dispenser by an individual tagged with the beacon tag device at the hand sanitizing station zone.

6. The wireless tracking system of claim 1, wherein:
the beacon tag device further comprises at least one of:
an audio output device configured to emit a sound;
an optical output device configured to emit light; and
a vibratory output device configured to emit vibration; and
if the second signal includes data pertaining to the hand hygiene non-compliance status, the beacon tag device is configured to at least one of:
emit the sound via the audio output device in a manner indicative of the hand hygiene non-compliance status;
emit light via the optical output device in a manner indicative of the hand hygiene non-compliance status; and
emit vibration via the vibratory output device in a manner indicative of the hand hygiene non-compliance status.

7. The wireless tracking system of claim 1, further comprising a gateway configured to communicate with:
the micro-zone transmitter device;
the beacon tag device; and
a server database.

8. A beacon tag device comprising:
a wireless receiver configured to receive a first signal including data pertaining to:
a unique identifier associated with a remote source of the first signal; and
a type of the remote source of the first signal, wherein the type is indicative of whether the remote source is configured to be deployed at a patient zone, an unsanitary zone, a hand washing station zone, or a hand sanitizing station zone;
a wireless transmitter configured to transmit a second signal of a frequency in an ISM band of between 2.4-2.485 GHz, wherein the second signal includes data pertaining to:
a unique identifier associated with the beacon tag device;
the unique identifier associated with the remote source of the first signal;
the type of the remote source of the first signal; and
either a hand hygiene compliance status or a hand hygiene non-compliance status associated with an individual tagged with the beacon tag device;
a processor configured to instruct the wireless transmitter to transmit the second signal; and
a motion detection sensor configured to detect at least one of movement of the beacon tag device and an impact to the beacon tag device and, in response thereto, output a wake-up signal to the processor, the wake-up signal causing the processor to transition out of a sleep-state or an off-state, wherein the processor is configured to instruct the wireless transmitter to transmit the second signal in response to receipt of the wake-up signal.

9. The beacon tag device of claim 8, wherein the first signal is of a frequency in at least one of a 902 MHz ISM band, a 915 MHz ISM band, an 869 MHz ISM band, an 894 MHz ISM band, and a 433 MHz ISM band.

10. The beacon tag device of claim 8, wherein the second signal further includes data pertaining to at least one of:
a unique identifier associated with the patient zone at which the remote source of the first signal is configured to be deployed;
a unique identifier associated with the hand washing station zone at which the remote source of the first signal is configured to be deployed; and
a unique identifier associated with the hand sanitizing station zone at which the remote source of the first signal is configured to be deployed.

11. The beacon tag device of claim 10, wherein the second signal further includes data pertaining to at least one of:
a status of the beacon tag device;
a power level of a power supply of the beacon tag device; and
an output of a sensor of the beacon tag device.

12. The beacon tag device of claim 8, further comprising at least one of a memory and a processor, wherein the at least one a memory and a processor is configured to have implemented thereat state machine logic utilized in determining the hand hygiene compliance status or the hand hygiene non-compliance status associated with the individual tagged with the beacon tag device.

13. The beacon tag device of claim 12, wherein the state machine logic is directed to hand hygiene compliance tracking in at least one of a patient interaction context and a bathroom context.

14. The beacon tag device of claim 8, wherein:
the beacon tag device further comprises at least one of:
an audio output device configured to emit a sound;
an optical output device configured to emit light; and
a vibratory output device configured to emit vibration; and
if the second signal includes data pertaining to the hand hygiene non-compliance status, the processor is further configured to at least one of:
instruct the audio output device to emit the sound in a manner indicative of the hand hygiene non-compliance status;
instruct the optical output device to emit light in a manner indicative of the hand hygiene non-compliance status; and
instruct the vibratory output device to emit vibration in a manner indicative of the hand hygiene non-compliance status.

15. A transmitter device comprising:
a wireless transmitter configured to transmit a first signal, the first signal includes data pertaining to a unique identifier associated with the transmitter device and a type of the transmitter device, wherein:
the type of the transmitter device is indicative of whether the transmitter device is configured to be deployed at a patient zone, an unsanitary zone, a hand washing station zone, or a hand sanitizing station zone;
a wireless transceiver configured to receive a second signal from a remote source, wherein the second signal is of a frequency in an ISM band of between 2.4-2.485 GHz; and
a processor configured to instruct the wireless transmitter to transmit the first signal.

16. The transmitter device of claim 15, wherein the first signal is of a frequency in at least one of a 902 MHz ISM band, a 915 MHz ISM band, an 869 MHz ISM band, an 894 MHz ISM band, and a 433 MHz ISM band.

17. The transmitter device of claim 15, wherein the first signal includes data that causes a beacon tag device configured to receive the first signal to emit at least one of sound, light, emit vibration in a manner indicative of a hand hygiene non-compliance status associated with an individual tagged with the beacon tag device.

18. The transmitter device of claim 15, wherein the transmitter device is configured to be deployed at only one of the patient zone, the unsanitary zone, the hand washing station zone, and the hand sanitizing station zone.

19. The transmitter device of claim 15, wherein the transmitter device is programmable to be deployed at any or all of the patient zone, the unsanitary zone, the hand washing station zone, and the hand sanitizing station zone.

20. The transmitter device of claim 15, wherein the transmitter device:
is configured to be deployed at the hand washing station zone; and
further comprises:
a proximity sensor configured to detect a physical presence of an individual at the hand washing station zone; and
a timer configured to track a time elapsed during detection of the physical presence of the individual at the hand washing station zone.

21. The transmitter device of claim 15, wherein the transmitter device:
is configured to be deployed at the hand sanitizing station zone; and
further comprises a pressure sensor configured to detect activation of a hand sanitizer dispenser at the hand sanitizing station zone.

22. The transmitter device of claim 21, wherein the transmitter device is configured to be integrated directly with the hand sanitizer dispenser.

23. The transmitter device of claim 15, wherein the wireless transmitter is configured with a programmable transmission power.

* * * * *